United States Patent
Keen et al.

(10) Patent No.: US 10,155,710 B1
(45) Date of Patent: *Dec. 18, 2018

(54) PROCESSES FOR MAKING C3 PRODUCTS FROM ETHYLENE AND SYNGAS USING HYDROFORMYLATION STRATEGIES

(71) Applicant: DP&PL LLC Series B, Houston, TX (US)

(72) Inventors: Brian T. Keen, Pinch, WV (US); Peter M. Loggenberg, Houston, TX (US); Donald C. Power, Houston, TX (US)

(73) Assignee: DP&PL LLC SERIES B, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,722

(22) Filed: Nov. 22, 2017

Related U.S. Application Data

(63) Continuation of application No. 14/962,476, filed on Dec. 8, 2015, now Pat. No. 9,856,198.

(Continued)

(51) Int. Cl.
  *C07C 45/50* (2006.01)
  *C07C 29/16* (2006.01)
  (Continued)

(52) U.S. Cl.
  CPC ............... *C07C 45/50* (2013.01); *C07C 1/24* (2013.01); *C07C 29/16* (2013.01); *C08F 110/06* (2013.01); *F25J 3/0238* (2013.01)

(58) Field of Classification Search
  CPC ......... C07C 29/16; C07C 45/50; C07C 47/02; C08F 110/06

(Continued)

(56) References Cited

U.S. PATENT DOCUMENTS

| 3,527,809 A | 9/1970 | Pruett et al. |
| 3,917,661 A | 11/1975 | Pruett et al. |

(Continued)

FOREIGN PATENT DOCUMENTS

| DE | 2354217 A1 | 5/1975 |
| WO | 03/024910 A1 | 3/2003 |

OTHER PUBLICATIONS

K. Weissermel and H.J. Arpe, "6. Syntheses involving Carbon Monoxide," Industrial Organic Chemistry, 2nd Edition (Weinheim), (1993) pp. 123-133.

(Continued)

*Primary Examiner* — Fred M Teskin
(74) *Attorney, Agent, or Firm* — Kagan Binder, PLLC

(57) ABSTRACT

The present invention relates to integrated processes for using hydroformylation reaction strategies to efficiently convert ethylene in ethylene feed mixtures into C3 products (i.e., products comprising 3 carbon atoms) such as propionaldehyde, 1-propanol, propylene, propanoic acid, and the like. An aspect of the present invention is to partially purify a feed comprising an ethane/ethylene mixture rather than to attempt more complete purification. In contrast to substantially complete purification of ethylene, partial purification is technically and economically feasible at lower cost and allows hydroformylation to be practiced at high productivity and with a lower hydrogen and CO requirement. The lower volumes of such syngas used in the hydroformylation reaction, as well as a more favorable profile of leftover reactants in following hydroformylation makes recycle strategies much easier to practice.

22 Claims, 10 Drawing Sheets

Related U.S. Application Data

(60) Provisional application No. 62/090,100, filed on Dec. 10, 2014.

(51) Int. Cl.
*C07C 1/24* (2006.01)
*C08F 110/06* (2006.01)
*F25J 3/02* (2006.01)

(58) Field of Classification Search
USPC .......................................... 568/451; 585/638
See application file for complete search history.

(56) References Cited

U.S. PATENT DOCUMENTS

| | | | |
|---|---|---|---|
| 4,148,830 A | 4/1979 | Pruett et al. | |
| 4,742,178 A | 5/1988 | Nelson et al. | |
| 4,769,984 A | 9/1988 | Raasch et al. | |
| 4,885,401 A | 12/1989 | Billig et al. | |
| 5,367,106 A * | 11/1994 | Unruh | C07C 45/50 568/451 |
| 5,475,183 A | 12/1995 | Araki et al. | |
| 6,049,011 A | 4/2000 | Kiss et al. | |
| 7,858,787 B2 | 12/2010 | Drent et al. | |
| 8,552,240 B2 | 10/2013 | Bailey et al. | |
| 9,856,198 B1 * | 1/2018 | Keen | C07C 45/50 |
| 2003/0176743 A1 | 9/2003 | Walz et al. | |
| 2005/0065389 A1 | 3/2005 | De Bruyn et al. | |
| 2014/0350305 A1 * | 11/2014 | Becker | C07C 45/50 568/454 |

OTHER PUBLICATIONS

B. Cornils, "The Hydroformylation Reaction Oxo Reaction/Roelen Reaction," J. Falbe, Ed. (Springer-Verlag, Berlin, 1980) pp. 3, 15, 16, and 18-21.

J. D. Unruh & L. Spinicelli, "n-Propyl Alcohol," Kirk-Othmer Encyclopedia of Chemical Technology, Third Edition, vol. 19 (1982) pp. 221-224.

* cited by examiner

PROCESSES FOR MAKING C3 PRODUCTS FROM ETHYLENE AND SYNGAS USING HYDROFORMYLATION STRATEGIES

PRIORITY CLAIM

This application is a continuation of U.S. application Ser. No. 14/962,476, filed Dec. 8, 2015, now U.S. Pat. No. 9,856,198, which issued on Jan. 2, 2018, which claims priority to U.S. Provisional Patent Application No. 62/090,100, filed Dec. 10, 2014, wherein the entirety of each of U.S. patent application Ser. No. 14/962,476 and U.S. Provisional Patent Application No. 62/090,100, respectively, is incorporated herein by reference for all purposes.

FIELD OF THE INVENTION

The present invention relates to processes in which C3 compounds (compounds including 3 carbon atoms such as propionaldehyde, 1-propanol, propanoic acid, propylene, etc.) are prepared from ethylene containing mixtures. More particularly, the present invention related to reacting ethylene-containing feed mixtures with gas mixtures containing CO and $H_2$ using hydroformylation strategies in order to produce one or more C3 products.

BACKGROUND OF THE INVENTION

Hydroformylation reaction strategies are widely known and have been well-documented over a span of many decades. Examples of literature that describes hydroformylation reactions include "New Syntheses with Carbon Monoxide", Ed. J. Falbe, Springer Verlag, New York, 1980, especially the Chapter "Hydroformylation, Oxo Synthesis, Roelen Reaction" by B Cornils; U.S. Pat. Nos. 3,527,809, 3,917,661, 4,148,830; 4,742,178, 4,769, 984, 4,885,401, 6,049,011, 8,552,240, and U.S. Patent Pub. No 2005/0065389, each of which is incorporated herein by reference in its respective entirety for all purposes.

Generally, hydroformylation involves reacting an unsaturated hydrocarbon with an excess of CO and hydrogen in the presence of a catalyst. Schematically, the reaction converts the double bond of the unsaturated hydrocarbon to a single bond, an H is added to the carbon atom on one side of the new single bond, and an aldehyde group, —C(O)H, is added to the carbon atom on the other side of the new single bond. Sometimes, small amounts of alcohol are also formed at this stage. Subsequent treatment techniques are used, as desired, to convert the aldehyde functionality into other functionality or to otherwise react the aldehyde with co-reactive functionality.

As a consequence of hydroformylation, an unsaturated compound containing "n" carbon atoms is converted into an aldehyde product containing "n+1" carbon atoms. For example, hydroformylation converts ethylene, a compound with 2 carbon atoms, into propionaldehyde, a compound with 3 carbon atoms. Hydroformylation causes the carbon chain to grow in length by one carbon atom. This is why hydroformylation has been described as a way to convert "lower" unsaturated hydrocarbons into a "higher" organic molecule.

Hydroformylation has been used to convert ethylene into propionaldehyde, which has then been converted into other C3 species such as propanol and propylene. This can be practiced using highly pure ethylene, e.g., from a mixture that is at least 99 weight percent ethylene. However, a substantial amount of commercially available ethylene is derived from feedstocks that, by their nature, contain both ethane and ethylene and thus are dilute in ethylene. Typically, such feedstocks result from processes in which the nature of the chemistry causes the feedstock to include no more than about 75 weight percent ethylene. It is difficult and expensive to purify these mixtures to obtain highly purified ethylene as might be desired for polyethylene manufacture due to the physical similarities between ethylene and ethane. Generally, using highly purified ethylene derived from such feedstocks is not an economically suitable way to practice hydroformylation of ethylene. This is particularly true in the case of shale gas recovery, where logistically isolated streams containing ethylene are expensive to purify due to the size of the resources and the lack of suitable pipelines.

Using the dilute ethylene mixtures also is problematic. Others have attempted this practice. See, e.g., U.S. Pat. No. 6,049,011. In these methods, the relatively expensive ethane is used to some degree to make ethylene, but overall the ethylene has low utilization. Impurities in the ethylene mixtures may also tend to poison and limit the expensive hydroformylation catalyst life/activity. In addition, other C3 and higher olefin impurities may lead to other undesirable by-products such as mixed aldehyde contaminates. The process also is inefficient in that relatively larger volumes of CO and hydrogen must be used to hydroformylate a dilute amount of ethylene effectively at an acceptable rate and degree of conversion. Also the excessive amounts of unreactive ethane and/or methane in the feed stream results in undesirably higher reaction pressures. This leads to relatively large purge streams leftover from the reaction that must be handled in some fashion. All of this adds substantial expense.

Consequently, even though hydroformylation techniques have been known and practiced for decades, the industry still needs a better way to practice hydroformylation of ethylene that is more efficient, more economical, and uses feed constituents with better utilization.

SUMMARY OF THE INVENTION

The present invention relates to integrated processes for using hydroformylation reaction strategies to efficiently convert ethylene in ethylene feed mixtures into C3 products (i.e., products comprising 3 carbon atoms) such as propionaldehyde, 1-propanol, propylene, propanoic acid, and the like. The present invention advantageously can use ethane feedstocks as at least one source for providing ethylene mixtures. Significant and sometimes excessive quantities of ethane are being generated from drilling and operating oil and natural gas wells. The excess ethane to a significant degree in some conventional practices is being converted to crude ethylene mixtures that are relatively dilute in ethylene, generally including no more than about 75 weight percent ethylene based on the total weight of hydrocarbons in the mixture. The mixtures are quite costly to further process in order to obtain highly pure ethylene. At the same time, there is a growing shortage of C3 products such as 1-propanol and in particular propylene to meet the needs of industry.

One surprising aspect of the present invention is how well C2 production strategies are coupled with C3 production strategies in a manner to efficiently use a high proportion of the raw materials and to help lower the cost of C2 and C3 production at the same time. Another remarkable innovation is the ability to integrate C2 and C3 production strategies to produce renewable C3 products. As used herein, "renewable" means that the C3 products are derived in whole or in part from renewable resources. Renewable resources generally encompass living organisms and include plants, animals (multi-cell organisms), and single cell organisms.

An important advantage of the present invention is that propylene or other desired C3 products may be derived in whole or in part from renewable resources in an efficient and effective manner. In preferred aspects, ethylene is derived from 100% renewable ethanol and/or ethane. In the meantime, all or a portion of CO and hydrogen can be derived from renewable resources. The renewable ethylene, renewable CO, and renewable hydrogen can be reacted in the presence of catalyst under hydroformylation conditions to prepare propionaldehyde. This in turn can be converted to other desired products, such as propylene. Significantly, this offers the opportunity to manufacture 100% renewable propylene which, in turn, allows for derivatives of propylene also to be renewable. As one example of a renewable synthesis strategy, at least 50 weight %, even at least 75 weight %, even at least 95 weight %, or even 100 weight % of renewable propylene can be made from a sugar cane or similar biomass by using the sugar from the plant to produce ethanol and using the biomass from the rest of the plant to produce CO and hydrogen (syngas). The renewable ethanol is converted to ethylene. The ethylene is reacted with the renewable syngas to form propionaldehyde. In illustrative renewable strategies, sugar cane bygasse is used to produce syngas and thereby effectively use this otherwise waste biomass.

This invention features an improved, integrated process to use these crude ethylene mixtures with more efficiency, higher productivity and higher utilization of ethane and other hydroformylation reactants in order to obtain one or more desired C3 products. The integrated system allows efficient use of raw materials, minimal ethylene raw material purification, simplified processing, and economical production of C3 products. The process allows the flexibility of efficiently producing C3 products from ethylene and/or ethylene mixtures containing ethane and/or hydrogen and/or CO and/or other hydrocarbons. The process also provides for higher utilization of hydrogen not only to accomplish hydroformylation but also to accomplish one or more other desired goals such as to convert propionaldehyde to propanol. For example, syngas production techniques may be used to produce hydrogen and CO used in hydroformylation. Theoretically, hydroformylation involves using 1 mole of $H_2$ and 1 mole of CO to convert 1 mole of ethylene to a C3 compound. Yet, syngas production often may produce substantial quantities of excess hydrogen relative to CO. Although at least a portion of this excess may be fed to the hydroformylation step, at least a portion of the excess optionally may be used to achieve one or more other desired objectives. For example, some of the hydrogen obtained from syngas production may be used to reduce propionaldehyde to 1-propanol. Theoretically, this reduction uses 1 mole of hydrogen per mole of propionaldehyde.

The scope of this invention extends to a variety of ethylene feed stocks of variable purity from a variety of sources. The technology allows efficient and high conversion of ethylene in the presence of ethane to propionaldehyde. This allows high ethylene utilization and high synthesis gas ("syngas") utilization without bearing the full cost of a more difficult and costly ethane/ethylene separation. Any unreacted ethylene and ethane are easily separated from C3 products such as propionaldehyde and propanol, and the C3 aldehyde product in turn is easily reduced to propanol and further dehydrated to propylene. The recovered ethane, along with any unreacted ethylene, may optionally be fed to syngas production to produce more CO and $H_2$ for the hydroformylation reaction, for propionaldehyde reduction, for use as a fuel, and/or recycled for ethylene production. The net result of such recycling is much higher utilization of reactants.

In some embodiments, the invention applies to hydroformylation of ethylene/ethane product mixtures sourced from ethane and/or ethylene produced from biomass ethanol using a variety liquid and/or gas phase technologies. In some embodiments, a portion of the ethylene used in hydroformylation is derived from crude ethylene mixtures and another portion is derived from biomass ethanol. In some embodiments, a majority and even substantially all of the ethylene used in hydroformylation is derived from biomass ethanol. Using at least some ethylene derived from biomass ethanol provides several advantages in the practice of the present invention. A first advantage relates to energy demand. Steam cracking of ethane to make ethylene as is typically practiced to obtain crude ethylene mixtures needs relatively high energy and yields products that generally contain less than 75 weight percent of ethylene based on the total weight of hydrocarbon content in the reaction mixture being dehydrogenated. The limit on ethylene content in the crude mixture is due in large part to equilibrium effects.

In contrast, much lower energy per amount of ethylene produced is used to convert ethanol into ethylene, and the conversion of ethanol into ethylene can occur with substantially 100% conversion. Using a combination of crude ethylene mixtures and ethylene derived from ethanol is desirable, because the resultant combination can include a higher concentration of ethylene than crude mixtures alone since the biomass-derived ethylene is substantially pure. The combination offers the opportunity to ease partial purification and make the overall process more energy efficient and economical. Yet, using only ethylene derived from biomass may not be desirable in some instances, inasmuch as the cost of using only ethylene derived from biomass may be too high to offset the benefits of using highly pure ethylene in the hydroformylation step. Moreover there is significant economic and process value in being able to use mixed ethylene feeds from multiple sources for hydroformylation enabled by the partial purification technology.

An important aspect of the present invention is to only partially purify a feed comprising an ethane/ethylene mixture rather than to attempt more complete purification. In contrast to substantially complete purification of ethylene, partial purification is technically and economically feasible at lower cost and allows hydroformylation to be practiced at high productivity and with a lower hydrogen and CO requirement. The lower volumes of such syngas used in the hydroformylation reaction, as well as a more favorable profile of leftover reactants in following hydroformylation makes recycle strategies much easier to practice.

In one aspect, the present invention relates to a method of using ethylene, comprising the steps of:
  (a) providing a feed mixture comprising ethane and ethylene;
  (b) partially purifying the feed mixture in a manner effective to provide a partially purified feed mixture comprising 80 to 98 weight percent of ethylene based on the total weight of hydrocarbons in the partially purified feed mixture and having less than 2 weight % C3 and higher hydrocarbons in the feed mixture based on the total weight of hydrocarbons in the feed mixture;
  (c) contacting the partially purified feed mixture with a gas mixture comprising hydrogen and carbon monoxide in the presence of a catalyst under hydroformylation conditions effective to convert at least a portion of the ethylene in the partially purified feed mixture into a product mixture comprising propionaldehyde and ethane;

(d) recovering a first product mixture portion from the product mixture, said first product mixture portion comprising a major portion of the propionaldehyde prepared in step (c); and (e) recovering a second product mixture portion from the product mixture, said second product mixture portion comprising a major portion of the ethane in the product mixture.

In another aspect, the present invention relates to a method of using ethylene, comprising the steps of:

(a) providing an ethylene feed mixture comprising 80 to 98 weight percent of ethylene based on the total weight of hydrocarbons in the feed mixture, wherein a first portion of the ethylene is derived from a renewable feedstock and an optional second portion of the ethylene is derived from ethane;

(b) contacting the feed mixture with a gas mixture comprising excess hydrogen and excess carbon monoxide in the presence of a catalyst under hydroformylation conditions effective to provide a product mixture comprising propionaldehyde, unreacted hydrogen, and unreacted CO;

(c) recovering a first product mixture portion from the product mixture, said first product mixture portion comprising a major portion of the propionaldehyde prepared in step (b);

(d) recovering a second product mixture portion from the product mixture, said second product mixture portion comprising a major portion of the unreacted CO and unreacted hydrogen in the product mixture; and (e) recycling and using at least a portion of the CO and hydrogen in the second product mixture portion in step (b); and wherein optionally substantially all of the ethylene used in step (a) is derived from at least one renewable resource; and wherein optionally substantially all of the hydrogen and carbon monoxide used in steps (c) and (d) are independently derived from one or more renewable resources; and wherein optionally substantially all of the reactants used in step (c) to prepare the propionaldehyde are derived from one or more renewable resources such that the propionaldehyde is a substantially 100% renewably sourced propionaldehyde.

In another aspect, the present invention relates to a method of using ethylene, comprising the steps of:

(a) using a first gas mixture comprising methane and ethane to make a second gas mixture comprising carbon monoxide and hydrogen;

(b) contacting a portion of the second gas mixture with a feed mixture comprising ethane and ethylene in the presence of a catalyst under hydroformylation conditions effective to prepare a product mixture comprising unreacted ethane and propionaldehyde, wherein the feed mixture comprises 80 to 98 weight percent of ethylene based on the total weight of hydrocarbons in the feed mixture;

(c) recovering a first product mixture portion from the product mixture, said first product mixture portion comprising a major portion of the propionaldehyde prepared in step (b);

(d) recovering a second product mixture portion from the product mixture, said second product mixture portion comprising a major portion of the ethane in the product mixture;

(e) using a portion of the hydrogen prepared in step (a) to convert at least a portion of the propionaldehyde in the first product mixture portion into propanol; and optionally recycling and using at least a portion of the ethane in the second product mixture portion to prepare a portion of the carbon monoxide and hydrogen in step (a).

In another aspect, the present invention relates to a method of using ethylene, comprising the steps of:

(a) providing a feed mixture comprising ethane and ethylene (b) partially purifying the feed mixture in a manner effective to provide a partially purified feed mixture comprising 80 to 98 weight percent of ethylene based on the total weight of hydrocarbons in the partially purified feed mixture and having less than 2 weight % C3 and higher hydrocarbons in the feed mixture based on the total weight of hydrocarbons in the feed mixture;

(c) contacting the partially purified feed mixture with a gas mixture comprising hydrogen and carbon monoxide in the presence of a catalyst under hydroformylation conditions effective to convert at least a portion of the ethylene in the partially purified feed mixture into a product mixture comprising propionaldehyde and unreacted ethane;

(d) recovering a first product mixture portion from the product mixture, said first product mixture portion comprising a major portion of the propionaldehyde prepared in step (c);

(e) recovering a second product mixture portion from the product mixture, said second product mixture portion comprising a major portion of the ethane in the product mixture; and (f) recycling and using at least a portion of the ethane in the second product mixture portion to prepare the feed mixture used in step (a).

In another aspect, the present invention relates to a method of purifying ethane from a mixture comprising ethane and ethylene, comprising the steps of:

(a) providing a feed mixture comprising ethane, ethylene, a light fraction, and a heavy fraction, wherein the light fraction comprises hydrogen, carbon monoxide, and methane, and wherein the heavy fraction comprises one or more hydrocarbons comprising three of more carbon atoms;

(b) partially purifying the feed mixture in a manner effective to separate a majority of the light fraction and a majority of the heavy fraction from the feed mixture and such that the partially purified feed mixture comprises 80 to 98 weight percent of ethylene and 1 to 20 weight percent ethane based on the total weight of hydrocarbons in the partially purified feed mixture;

(c) contacting the feed mixture with a gas mixture comprising hydrogen and carbon monoxide in the presence of a catalyst under hydroformylation conditions effective to provide a product mixture comprising propionaldehyde and unreacted ethane;

(d) recovering a first product mixture portion from the product mixture, said first product mixture portion comprising at least 96 weight percent of the ethane in the product mixture based on the total weight of ethane in the product mixture;

(e) recovering a second product mixture portion from the feed mixture, said second product mixture portion comprising a major portion of the propionaldehyde;

(f) using at least a portion of the ethane in the first product mixture to prepare at least a portion of the ethylene used in step (a).

Advantageously, this further aspect of the invention helps to lower the cost of ethylene production in processes that currently produce specification polymer grade ethylene by integrating ethylene and C3 production by effectively raising unit capacity and reducing energy requirements of existing equipment. For example, an existing distillation column may be used in a conventional way to prepare high purity ethylene from such a feedstock at a certain throughput. By using the existing column to prepare partially purified ethylene instead of highly pure ethylene, the throughput can be increased by a factor of at least two, or even at least 3 according to simulations of distillation column performance. This further aspect also allows higher unit utilization by providing the opportunity to produce a flexible and more valuable product mixture obtained from hydroformylation. Advantageously, this strategy allows hydroformylation equipment to be easily added to an existing distillation unit with higher throughput to increased volume of more valuable product streams to be produced.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Figure 1:
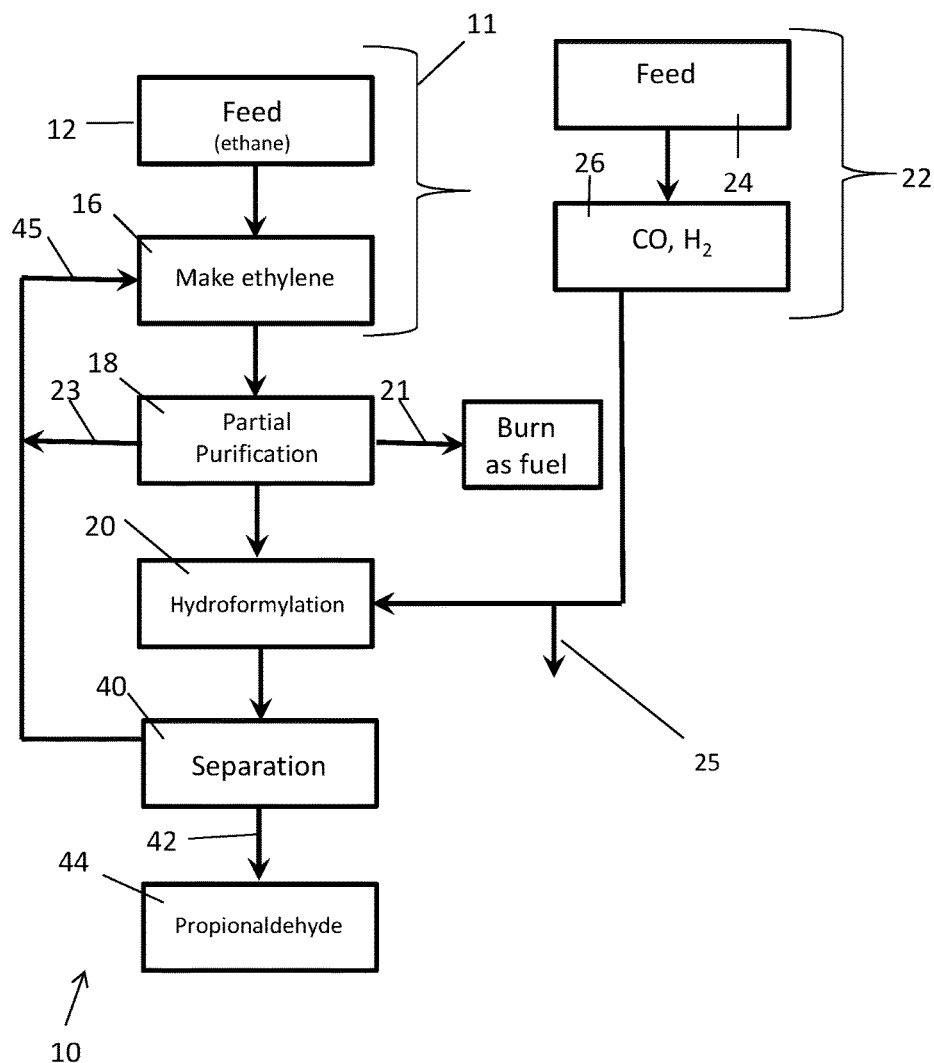
FIG. 1 schematically shows a flow chart of one embodiment of a process of the present invention in which a feedstock containing ethane is converted into a C3 product, which in this embodiment is propionaldehyde.

FIG. 1 schematically shows a flow chart of one embodiment of a process of the present invention in which a feedstock comprising ethane is converted into a C3 product, which in this embodiment is propionaldehyde. As used herein, a C3 product refers to a compound having 3 carbon atoms. Examples include propionaldehyde, propane, propylene, substituted derivatives of these, and combinations thereof. Examples of substituents include OH, halogen, O, and combinations of these. In some modes of practice, an exemplary substituent is OH, and a substituted C3 product comprises 1-propanol. The process of FIG. 1 is particularly useful for making propionaldehyde, $CH_3CH_2C(O)H$. The process of FIG. 1 also can include optional process features in order to make other C3 products such as 1-propanol and/or propylene and/or 2-propanol (isopropanol). The process of FIG. 1 can be practiced on small scale for laboratory practice, on a moderate scale for pilot plant practice, or on a large scale for production of commercial quantities of one or more C3 products.

In a first step 11, comprises providing an ethylene feed mixture (also referred to herein as a "crude" ethylene feed mixture) that typically comprises 10 to 75 weight percent of ethylene based on the total weight of hydrocarbons in the ethylene feed mixture. As used herein, a hydrocarbon is any compound that contains at least one C atom and at least one hydrogen atom. Hydrocarbons may be linear, branched, or cyclic; aromatic or aliphatic; substituted or unsubstituted; ionic or nonionic, and/or saturated or unsaturated. Ethylene (also referred to as ethene) is an unsaturated C2 (C2 refers to a compound having 2 carbon atoms) hydrocarbon with the formula $C_2H_4$.

Many advantages result from using a crude ethylene feed mixture in the practice of the present invention. First, such mixtures comprising predominantly ethylene and ethane are economically prepared using commercial scale processes. This makes the crude feed very useful in large scale production of C3 products. Further, the present invention provides advantageous process features that allow such a crude feed mixture to be used in hydroformylation reaction schemes to produce C3 products at very high yield much more economically and using less energy overall than by using only high purity ethylene feedstocks, e.g., ethylene feed mixtures that are greater than 99.5 weight percent ethylene. One important aspect is to partially purify the crude ethylene feed mixture prior to hydroformylation, discussed further below. Other important aspects involve recycle strategies that dramatically improve efficiency, yield and overall economics.

The crude ethylene feed mixture of step 11 may be provided in a number of different ways. According to one approach as shown in FIG. 1, the crude ethylene feed mixture is provided by a method comprising two stages. In a first stage shown as step 12, a feed comprising ethane or predominately ethane is provided. The ethane provided in step 12 can be derived from a variety of different sources. For example, if desired, ethane can be procured from one or more commercial sources. As an option in those modes of practice that use ethane, significant quantities of ethane are generated from drilling and operating oil and gas wells, and this generated ethane is an excellent, economic source of ethane. Other commercial processes also may generate excess ethane as a by-product of hydrocarbon purification, and such ethane is another excellent, economic source of ethane. Ethane also may be produced from renewable feedstocks. Examples of such feedstocks include corn, sugarcane, bagasse, sugar beets, potatoes, corn stover, municipal solid waste, other biomass sources, and combinations of these. Ethane can be made using a variety of well-known processes, including fermentation, enzymatic production, bacterial production, or other chemical synthesis.

In a second stage shown as step 16, the ethane is converted into the crude ethylene feed mixture. In addition to ethylene, the crude product mixture also contains unreacted ethane. A typical crude product mixture may contain 2 to 400 parts by weight, preferably 10 to 100 parts by weight, more preferably 10 to 50 parts by weight of ethane per 100 parts by weight of ethylene.

An exemplary process for converting ethane into ethylene involves steam cracking of ethane. Steam cracking generally involves diluting ethane with steam and heating the mixture to very high temperatures, e.g., often 900° C. or higher. Under such conditions, the saturated ethane is converted to the unsaturated ethylene plus some hydrogen. Ethane is a very desirable reactant to use for ethylene production because steam cracking of ethane is highly selective for making ethylene. Although other hydrocarbons may be used as a starting point for ethylene production, steam cracking of those materials generally is less selective, and more by-products tend to result.

Due to the nature of the steam cracking conversion of ethane to ethylene, the process tends to produce crude ethylene product mixtures containing 10 to 78 weight percent, often 30 to 76 weight percent, or even 40 to 74 weight percent of ethylene based on the total weight of hydrocarbons in the product mixture. Often, the mixture also contains hydrogen as a by-product of the reaction. Other impurities or by-products also may be present. Examples of other impurities and/or by-products include CO, $CO_2$, methane, acetylene, and saturated and unsaturated hydrocarbon compounds containing 3 or more carbon atoms. The components of the admixture that are more volatile than ethylene are referred to generally as the "light components." The light components include hydrogen, CO, $CO_2$, and methane. The compounds containing 3 or more carbon atoms may be referred to as the "heavy components."

Although the inability of steam cracking as conventionally practiced to produce more pure ethylene is a potential drawback, the present invention provides strategies that makes these crude mixtures highly effective in hydroformylation reaction strategies to produce C3 products economically at high yield. Steam cracking of ethane to form ethylene is further described in PEP Report 29E P. 6.4-6.8 (JJLM) 1E-430 and Process Economics Program Report No. 29C July 1985; and Process Economics Program Report No. 29E Ethylene, October, 1991.

An exemplary product composition resulting from steam cracking ethane to produce ethylene is shown in the following table, which shows the proportions of the constituents with respect to the molar percentage, weight percentage based on the total weight of the product composition, and weight percentage based on the total amount of hydrocarbons in the composition:

|  | Ethane Steam Cracking Product Mole % | Ethane Steam Cracking Product Weight % | Wt % on Hydrocarbon Only Basis |
|---|---|---|---|
| Hydrogen | 46.6 | 5.9 | |
| CO | 0.3 | 0.5 | |
| Acetylene | 1.2 | 2.0 | 2.1 |
| Methane | 7.8 | 8.0 | 8.6 |
| Ethylene | 37 | 66 | 70.6 |
| Ethane | 4.8 | 9.2 | 9.8 |
| Propane + Propylene + Propadiene | 0.5 | 1.4 | 1.4 |
| Butadiene + Butanes | 1.1 | 3.9 | 4.2 |
| >C4 | 0.7 | 3.1 | 3.3 |
| Total | 100 | 100 | 100 |

The hydroformylation step 20 occurring after step 18 is highly tolerant to hydrogen and to some extent, methane and ethane that may be present in the crude ethylene feed mixture. The ability of step 20 to tolerate ethane is one reason that partial purification can be effectively practiced according to principles of the present invention. However, other materials such as unsaturated hydrocarbons containing 3 or more carbon atoms, oxygen, halogen containing species, sulfur containing species, nitrogen containing species, and the like, could have a tendency to poison hydroformylation catalysts or otherwise inhibit the effectiveness of the hydroformylation reaction carried out in step 20. Accordingly, the crude ethylene product mixture desirably is treated to remove such other materials. Except with respect to the partial purification pursuant to step 18, other species may be optionally allowed to remain.

The crude ethylene feed mixture obtained in step 16 will generally comprise both ethylene and ethane. Being that the ethylene content is generally no more than about 75 weight percent of the mixture resulting from practicing preferred steps 12 and 16, a potential option is to purify the mixture to obtain highly pure ethylene. This would involve separating ethylene from the remaining ethane. This is a challenging and costly separation because chemically and in terms of molecular weight, ethane and ethylene are very similar. If a goal were to practice this separation in a manner effective to obtain highly pure ethylene (e.g. a product mixture in which 99.9 weight percent or more of the mixture is ethylene), the separation would add significant additional cost to the production, by way of increased unnecessary capital equipment cost and energy costs.

On the other hand, using a crude feed mixture that is too dilute in ethylene makes the hydroformylation stage in step 20 and/or handling the output of hydroformylation more difficult. In particular, as described below, hydroformylation is generally practiced by reacting ethylene with a gas mixture (often referred to as "syngas") comprising hydrogen and CO. A certain concentration (e.g., partial pressure) of syngas relative to the total amount of the crude ethylene feed mixture is needed for the hydroformylation to be carried out as effectively or at as high a rate and conversion as might be desired. When the crude ethylene feed mixture is relatively dilute, a relatively large amount of syngas is needed for the volume of crude feed mixture being used even though the ethylene content of that mixture might be relatively dilute. In other words, excessive amounts of syngas would be used to carry out a hydroformylation reaction with a relatively small amount of ethylene. This is difficult to accomplish, because a significant portion of the available reactor pressure is occupied by ethane. Such a process will end up with a substantial amount of excess syngas as well as excess ethane and unreacted ethylene to purge or otherwise handle after hydroformylation. Moreover ethylene conversion will tend to be depressed. The amount of ethane in such a purge stream makes it problematic to recycle the purge stream, because the C to H ratio in the recycle may be too low to provide a suitable syngas for hydroformylation without undue expense or treatment.

The significant challenge, therefore, is that fully purifying the crude ethylene mixture is not economical, and using the crude ethylene feed mixture without any purification poses technical and economic challenges. The present invention provides an innovative solution in which the crude ethylene feed mixture is partially purified in step 18 in a manner effective to provide a partially purified feed mixture comprising 80 weight percent to 98 weight percent, preferably, 85 to 98 weight percent, most preferably 90 to 98 weight percent ethylene based on the total amount of hydrocarbon in the partially purified feed mixture. Additionally, it also is preferred that at least 90 weight percent, preferably at least 95 weight percent, and more preferably at least 99 weight percent of the olefin content of the partially purified ethylene feed mixture is ethylene.

In exemplary modes of practicing the present invention, partial purification according to step 18 comprises treating the crude ethylene feed mixture of step 16 in a manner effective to remove 99 weight percent or more of the light components, a portion of ethane, at least a portion of acetylene, and 99 weight percent or more of the C3 and higher saturated and unsaturated hydrocarbons. Desirably, the partially purified ethylene feed mixture has less than 2 weight %, preferably less than 1 weight %, more preferably less than 0.5 weight percent, even more preferably less than 0.05 weight percent C3 and higher hydrocarbons in the feed mixture based on the total weight of hydrocarbons in the feed mixture. Typically at least some of the ethane and/or acetylene may be removed by partial purification. In illustrative embodiments, the partially purified ethylene feed mixture has a weight ratio of ethane to ethylene in the range from 1:70, preferably 1:4. Prior to partial purification, the crude ethylene feed mixture may comprise a large relative amount of ethane. For instance, in some embodiments, the weight ratio of ethane to ethylene in the crude ethylene feed mixture is in the range from 1:10 to 4:1.

A variety of different treatments may be used to accomplish partial purification of a crude ethylene mixture obtained by steam cracking ethane. FIG. 10 schematically shows a more specific embodiment of a partial purification strategy for practicing step 18 of FIG. 1. The partial purification strategy of FIG. 10 also may be used in the practice of other embodiments of the present invention, including in any of the process embodiments described in FIGS. 1-9.

As shown in FIG. 10, the crude ethylene mixture of step 16 is subjected to the partial purification treatment of step 18. According to this embodiment, partial purification occurs in three stages shown as stages 18a, 18b and 18c. As an option, this mixture may be treated to hydrogenate the acetylene to ethylene. Additionally, hydrogen may be removed by a technique such as membrane separation. According to step 18a, the crude ethylene mixture resulting from step 16 is treated to remove substantially all of the light and heavy components in purification substeps 18a and 18b of the partial purification step 18. Desirably, partial purification is practiced under conditions effective to remove at least a majority (i.e., at least 50 weight percent), even at least 80 weight percent, preferably at least 90 weight percent, more preferably at least 95 weight percent, and even more preferably at least 99 weight percent of the light and heavy components in the crude ethylene mixture based on the total weight of the light and heavy components. This is relatively easy to accomplish using a variety of techniques inasmuch as the light and heavy components have volatilities substantially different from the volatilities of ethane and ethylene. Optionally hydrogenation may be practiced to reduce dienes and acetylene prior to carrying out the hydroformylation step 20.

An exemplary technique for separating a light fraction from the crude ethylene mixture is practiced in step 18a to allow the light fraction to be withdrawn as stream 202 while the remainder of the crude ethylene mixture is withdrawn as stream 204. Step 18a may be accomplished by first removing a major portion of the hydrogen (not shown) by a suitable technique such as membrane separation. After hydrogen is removed, the stream is then compressed and vaporized to obtain streams 202 and 204. The crude ethylene mixture introduced to step 18a is more easily compressed and vaporized when a major portion of the hydrogen is removed first. Because the light fraction (often including hydrogen, CO, $CO_2$, and methane) are so much more volatile than the other constituents of the mixture, the compression and vaporization treatment allows at least a majority of the light fraction to be separated and withdrawn via stream 202. In many embodiments, separating at least 99 weight percent of the light fraction constituents is practical to achieve.

Stream 204 is then treated according to step 18b to separate and withdraw stream 210 that includes at least a majority of the heavy fraction constituents of the crude ethylene mixture obtained from step 16. The resultant partially purified ethylene can be recovered and fed to step 20 for hydroformylation.

An exemplary technique for removing the heavy fraction as stream 210 includes distillation. Because the boiling point differences between C3 and higher constituents, on the one hand, and ethane and ethylene on the other hand, are so large, separating the heavy constituents from ethane and ethylene is accomplished economically and in a straightforward manner using distillation techniques. The feed often is chilled and pressurized. For example, supplying the feed at a temperature in the range from −25 F to 15 F, preferably −10 F to 10 F at a pressure in the range from 300 psia to 1000 psia, preferably 350 psia to 600 psia would be suitable. The distillation column is operated under conditions effective to provide an ethylene and ethane rich stream at the top of the column and $C3^+$ stream taken from the bottom of the column. Optionally, the tower may be operated at a reflux ratio in the range from 0.3 to 3. For example, the refrigeration duty of the column may be in the range from 10 to 50 MM btu/hr. For example, a suitable distillation tower may have 10 to 55 theoretical stages and be 20 to 110 feet tall.

Advantageously, the light and/or heavy streams 202 and 210 may be further processed and/or recovered for further use. For example, the light component stream 202 typically may include hydrogen, methane and CO, and $CO_2$. As an option, this stream may be subjected to a treatment in optional step 205 to remove at least a portion of the hydrogen as stream 207. The hydrogen in stream 207 may then be used in any desired manner. For example, stream 207 may be used to reduce propionaldehyde to 1-propanol according to step 50 in any of FIGS. 5 to 9. All or a portion of stream 202 also may be used as stream 206 which is fed to step 24 in any of FIGS. 1-9 to be used as a feed for syngas production and/or as stream 208 to be burned as fuel in step 209. As still yet another option, all or a portion of the hydrogen, methane and/or CO containing stream 202 can be fed forward (not shown) to be used in the hydroformylation step 20.

The stream 210 containing at least a majority of the heavy constituents can be used in one or more different ways as well. For example, all or a portion of stream 210 may be withdrawn as stream 211 and optionally be burned as fuel. If burned as fuel, the heat energy can be used in the current process or other processes. As another option, all or a portion of stream 210 may be withdrawn as stream 212 in order to purify the heavy constituents in step 214. As another option, all or a portion of stream 210 may be withdrawn as stream 216 and recycled to step 16 to make more ethylene via steam cracking or other suitable technique.

Because the light and heavy components are easily separated from the ethane and ethylene, the resultant crude mixture recovered as stream 215 after such separations according to steps 18*a* and 18*b* is predominantly a mixture of ethylene and ethane. Typically, the resultant crude stream 215 includes less than 1 weight percent of light and heavy constituents at this stage, based on the total weight of stream 215. Stream 215 is then treated in step 18*c* to obtain a partially purified ethylene stream having a weight ratio of ethane to ethylene in the range from 1:4, to preferably 1:50. Whereas using distillation techniques to obtain highly pure ethylene from an ethylene/ethane mixture is more demanding in terms of energy demand and equipment size, distillation is quite effectively and economically practiced to obtain partially purified ethylene from such a mixture. Examples 6 and 7 illustrate the advantages of partial purification in terms of energy and equipment demands relative to more complete purification. Optionally, steps 18*b* and 18*c* could be combined into a single step and carried out at the same time.

Step 18*c* may be accomplished by distillation in representative modes of practice. In a typical distillation, the mixture including ethylene and ethane is fed to a distillation column. The feed often is chilled and pressurized. For example, supplying the feed at a temperature in the range from −25° F. to 15° F., preferably −10° F. to 10° F. at a pressure in the range from 300 psia to 1000 psia, preferably 350 psia to 600 psia would be suitable. The distillation column is operated under conditions effective to provide an ethylene rich stream at the top of the column and an ethane rich stream taken from the bottom of the column. In FIG. 10, the ethane rich stream is withdrawn as stream 220, and the ethylene rich stream is withdrawn as stream 228. For example, an ethylene rich stream may be recovered at a temperature in the range from −25° F. to 15° F., preferably −15° F. to 0° F. at a pressure of 300 psia to 500 psia. For example, an ethane rich stream may be recovered at a temperature in the range from 25° F. to 35° F. at a pressure from 300 psia to 500 psia. For example, the tower may be operated at a reflux ratio in the range from 2 to 5. For example, the refrigeration duty of the column may be in the range from 30 to 50 MM btu/hr. For example, a suitable distillation tower may have 15 to 55 theoretical stages.

The ethane rich stream 220 may be recycled and/or used in one or more different ways. For example, the ethane rich stream 220 may be recycled back via stream 222 to use in steam cracking to prepare more ethylene in step 16 (FIG. 1-9). As another option, some or all of the ethane rich stream 220 may be withdrawn as stream 224 and used to create syngas in step 24 (FIGS. 1-9), although generally it is desirable to limit the ethane content of the feed used to make syngas, as the syngas reaction may be more exothermic than desired if the content of the ethane in the reaction feed is too high. As general guidelines a feed suitable for syngas production may contain from 1 to 10 parts by weight of ethane to about 100 parts by weight methane in many modes of practice. The ethylene rich stream 228 is fed to the hydroformylation step 20 (FIGS. 1-9).

In addition to the partial purification strategy shown in FIG. 10, other strategies also may be used to accomplish partial purification of a crude ethylene feed mixture. As one example the partial purification of a crude ethylene mixture obtained from an ethane cracker could be accomplished cost effectively by exploiting Joule/Thompson effects. Joule/Thomson effects relates to the temperature changes of gases or liquids when forced through a valve, porous plug, or other orifice while kept insulated to minimize heat that is exchanged with the environment. Joule/Thomson effects are used in the oil industry to separate methane from mixtures of methane, ethane, propane, and butane. According to conventional oil industry practice, natural gas is compressed and cooled. The mixture is expanded generally adiabatically to cool it further. This condenses the ethane/propane/butane without the need for further refrigeration, while the methane can be withdrawn as a vapor. Using only a few stages in a separation column, methane is produced with less than 3 weight percent % ethane. Purified ethane may be recovered as a second stream. Additionally, a third stream containing ethane, propane, and butane may be recovered as a third stream which contains about 40% ethane. This works well in the oil industry application, at least in part because the ethane/propane/butane are non-ideal gases and as such cool more on expansion than predicted by the ideal gas law.

The same principles may be applied to partially purify a crude ethylene mixture in the practice of the present invention. Initially, a crude ethylene mixture is obtained from an ethane cracking treatment. As an option, this mixture may be treated to hydrogenate the acetylene to ethylene and ethane. Additionally, hydrogen may be removed by a technique such as membrane separation. The resultant mixture may then be compressed and cooled via generally adiabatic expansion to allow direct recovery of a partially purified ethylene stream, e.g., a stream comprising 88 weight % ethylene and substantially all of the remainder of the stream being ethane. This stream is fed to hydroformylation in step 20 (FIGS. 1-9). It is very likely that a partially purified ethylene column could be run using this effect. In contrast, using the Joule Thomson effect is impractical for a high purity ethylene column due to the large quantities of refrigeration required. The purge stream comprising ethane withdrawn from the hydroformylation step also may be subjected to a Joule/Thompson treatment to recover ethane from the purge stream. The ethane may be recycled back to the ethane cracker to make ethylene in step 16. The residual ethylene in this recycled ethylene stream could be hydrogenated back to ethane as an additional option.

Distillation is another strategy that can be used to accomplish partial purification of a crude ethylene feed stream obtained by steam cracking ethane. An illustrative crude ethylene feed stream might include a formulation including ethylene, ethane, propylene, propane, cis-butylene, butane, 2-methyl-1-butene. The feed stream is fed to a distillation column. Any feed rate could be used. For example, a feed rate on a commercial scale might be 500 to 300,000 pounds per hour. An exemplary feed rate is 125,000 lb/hr. The feed may be supplied at a suitable temperature and pressure. For example, the temperature of the feed may be in the range from −25 F to 15 F, preferably −5 to 10 F in many embodiments. An exemplary feed temperature is 8 F. For example, the pressure of the feed may be in the range from 300 psia to 1000 psia. An exemplary feed pressure is 450 psia.

The distillation column has characteristics effective to allow a partially purified ethylene stream to be recovered from the top of the column. For example, a suitable column would have 10 to 40 theoretical stages, a diameter of 2 feet to 20 feet, a reflux ration of 0.3 to 3, a refrigerator duty of 10 to 50 MM BTU/hr, and a tray section height of 10 to 70 feet. An exemplary distillation column has 20 theoretical stages, a diameter of 10 feet, a reflux ration of 1.4, a refrigerator duty of 18.6 MM/BTU/hr, and a trayed section height of 40 feet.

A partially purified stream of ethylene is recovered from the top of the column. This may be recovered at a suitable temperature, pressure and flow rate. An illustrative partially purified ethylene stream comprises 91.1 weight percent ethylene. The partially purified ethylene stream may be fed directly to the hydroformylation step 20. Since the hydroformylation process can feed vaporized ethylene, the liquid ethylene from the partial purification column is re-vaporized to supply refrigeration capacity to the column. A heavy stream is recovered from the bottom of the distillation column. The heavy stream may be further handled in a variety of ways. For example, the heavy stream may be processed using one or more of the options used with respect to stream 220 in FIG. 10.

In addition to the partial purification strategy shown in FIG. 10, another preferred strategy also may be used to accomplish partial purification of a crude ethylene feed mixture. The ethylene distillation column in a conventional ethane steam cracking unit in the past has been operated to produce specification grade ethylene (>99.9 wt % ethylene) as might be required typically for polyethylene and/or ethylene oxide production. Used in this way, this piece of equipment is a high capital expense item, uses a relatively large amount of energy for the amount of separation achieved, and limits the overall production rate of the plant. According to the present invention, choosing to lower the ethylene purity requirement to 95 wt % or even 90 wt % for partial purification results in a very significant increase in the ethylene production capacity. At the same time, using the column for partial purification further results in a significant lowering of the energy consumption and thereby cost of operating the separation. Moreover, this productivity change results in a significant lowering of the overall cost of ethylene production. As described below in Example 9, a typical high purity ethylene distillation column would have roughly three times its design capacity if it was operated to produce 91.3 wt % purity ethylene. The simulation described in Example 10 below shows that the same typical ethylene distillation column would have 51% more capacity producing 95 wt % ethylene as compared to producing 99.9 wt %. The simulations also shows that a typical 99.9 wt % ethylene purity column will consume 46.3 mm btu/hr of refrigeration as compared to 16 mm btu/hr to produce 91.3 wt % ethylene and compared to 27.9 mm btu/hr to produce 95 wt % ethylene.

Partially purifying the crude ethylene feed mixture provides many advantages. In combination with recycle strategies described herein, partial purification allows very high usage of ethane to make ethylene at lower cost. In particular partial purification requires dramatically less equipment and energy costs. This translates to lower facility capital cost. The lower capital cost opens up the option of practicing the technology at gas gathering/compression sites enabling use rather than flaring of excess ethane. Partial purification is economical and easy to accomplish. The resultant partially purified mixtures are very effectively used to produce C3 products. The extra expense and effort needed to provide highly purified ethylene is not needed. The higher concentration of ethylene in the partially purified feed mixture provides higher efficiency, higher reaction rate, higher conversion, and higher productivity in the hydroformylation reaction of step 20. These advantages generally are enhanced by further removing contaminants that could poison or otherwise impair the catalysts used in step 20. These catalyst poisons can be removed at any stage upstream form step 20 as desired. The volume of syngas that is purged following hydroformylation relative to the ethylene converted to C3 products is greatly reduced. Moreover, the reduced ethane content in the purge stream resulting from hydroformylation allows that purge stream to be used in one or more different recycle strategies that allow the relatively expensive ethane reactant to be used more efficiently to produce more ethylene and/or more syngas reactant, as desired. An important feature that allows the purge to be recycled to make more syngas is that the ethane content of the purge is low relative to the amount of syngas needed.

The term "syngas" refers to a gas mixture comprising CO and hydrogen. The mixture might also include other ingredients such as methane, carbon dioxide and water. The term "syngas" is used in industry to refer to the common use of this fluid mixture to produce synthetic natural gas and liquid hydrocarbons. Syngas units useful to prepare syngas are commercially available from sources including the Air Liquide Group (Houston, Tex.), Linde Engineering (Blue Bell, Pa.), and the like. Making syngas from ethane or mixtures of ethane and methane is less efficient than making syngas from methane as the reaction may be more exothermic than is desired when too much ethane is present. Further, adequate quantities of hydrogen may not be produced to supply both hydroformylation and hydrogenation of the propionaldehyde to propanol.

The difficulty of using too much ethane to make syngas is another reason why the partial purification strategy of the present invention is so advantageous. Without partial purification, the purge gas resulting from hydroformylation generally could be too rich in ethane. This limits amount of the purge suitable for use as a recycle to make more syn gas and/or imposes the need to remove ethane from the purge to make the recycle more suitable for syngas production. Also, the relatively high amount of excess CO and $H_2$ in the purge makes the purge hard to handle as an ethane recycle stream to make more ethylene. Partial purification alleviates both of these issues. In a purge stream resulting from partial purification, the ethane content is sufficiently reduced to allow all or a portion of the purge to be recycled so that the ethane can be used to make more syngas more easily with reduced concern that the recycled material will make syngas operations more exothermic than desired. Additionally, the overall volume of the purge is sufficiently low that all or a portion of the purge can be recycled to use the ethane to make more ethylene. The result of practicing one or both kinds of recycle strategies is that the ethane, a relatively expensive reactant, is used with much improved utilization.

Partial purification is much easier to practice than more complete purification. For example, theoretical calculations indicate that only about 30 separation stages in a separation apparatus are needed to partially purify ethylene up to 98% pure. In contrast, calculations indicate that 200 or more separation stages would be needed to achieve 99% or greater purity ethylene.

Referring again to FIG. 1, the partially purified ethylene feed mixture resulting from step 18 is then used to provide ethylene as a reactant in the hydroformylation reaction stage of step 20. In addition to the primary, partially purified ethylene stream fed from step 18 to step 20, step 18 also produces one or more side streams containing one or more materials that were separated from the primary stream. Examples of materials typically present in the one or more side streams include hydrogen, methane, carbon monoxide, carbon dioxide, ethane, acetylene and hydrocarbons including 3 or more carbon atoms. According to industry terminology, the hydrogen, methane, carbon monoxide, and carbon dioxide are referred to as the light components and when separated from the mixture are referred to as the light(s) stream or light fraction. The hydrocarbons including 3 or more carbon atoms are referred to as the heavy components and when separated from the mixture ar referred to as the heavy(ies) stream or fraction. These side streams may be handled in any desired fashion. As one option (not shown), the side streams from step 18 may be discarded. As another option shown via stream 21, the side streams may be burned as fuel to provide heat energy. As another option shown via stream 23, the side stream materials may be recycled to stream 45 and used to make more ethylene. As still another option (not shown), hydrogen in the side stream(s) may be separated using a suitable technique (e.g., membrane separation) and carried forward to reduce the propionaldehyde product of step 44 to reduce the propionaldehyde to 1-propanol. At least a portion of the lights stream preferably could be co-fed to the syngas production process.

Optional treatments to help make ethylene feed mixtures more suitable for hydroformylation have been described in U.S. Pat. No. 6,049,011. As one option, the ethylene feed mixture may be treated before hydroformylation to remove all or a portion of catalyst poisons (e.g., sulphur-, nitrogen- and chlorine-containing compounds, and oxygen), if present, or reduce them to a level at which catalyst life is economically acceptable. As another option, higher boiling hydrocarbons, e.g., C3+(i.e., 3 or more carbon atoms) may be removed from such a feedstream source prior to hydroformylation. Such optional treatments, if any, may be implemented before and/or after partial purification to remove a portion of the ethane content is practiced. A variety of different treatments may be practiced to remove the higher boiling (C3+ hydrocarbons) components and other catalyst poisons. Examples of techniques include, for example, reactive separation (e.g., caustic wash), catalytic conversion (e.g., hydrogen) or fixed bed adsorption (e.g., ZnO), distillation, absorption, combinations of these, and the like.

Desirably, the partially purified ethylene feed mixture is treated as a stage of partial purification under conditions such that at most 1 weight percent, constitutes such higher boiling species. Also desirably, the feed mixture is treated so that at most 1.0 weight percent constitutes acetylene and at most 10 weight percent, preferably at most 5 weight percent constitutes molecular nitrogen. Also desirably, treatment is effective so that the total amount of sulphur-, chlorine- and nitrogen-containing compounds is at most 1 ppm on a weight basis. Further, the level of oxygen desirably is at most 10 ppm on a weight basis.

Many other species present in the ethylene feed mixture such as hydrogen, ethane remaining after partial purification, ethanol, or the like, may be allowed to remain, thereby minimizing the need for and cost of cryogenic separation often used in manufacture of high purity ethylene, or hydrogenation under severe conditions to remove the acetylene produced by pyrolysis. Hydroformylation generally may tolerate certain C3 species that might be present, wherein the C3 species is generally free of amine, thio (sulfur containing), or other functional groups that might unduly hinder function of hydroformylation catalysts. For example, unsaturated C3 species, such as propylene are undesirable at this stage, as they may result in by-product, contaminant C4 aldehydes during the hydroformylation process. On the other hand, some C3 species such as propionaldehyde are suitable hydroformylation solvents.

Syngas also is provided to the hydroformylation reaction of step 20. The ratio of $H_2$ to CO in the syngas used for hydroformylation is desirably in the range from 1.1:1 to 1.01:1, preferably 1.06:1 to 1.02:1. Often, syngas may be made or otherwise initially provided in a manner such that the ratio of hydrogen to CO is much higher than this. The excess hydrogen can be separated and used in other reaction stages as desired. For example, the excess hydrogen may be used to reduce propionaldehyde to propanol. In some modes of practice, syngas in the practice of the present invention is anhydrous.

Syngas may be provided for use in step 20 in a variety of different ways. According to one illustrative mode of practice, CO from a first source and $H_2$ from a second source may be combined to provide the syngas mixture. As another option, as shown in FIG. 1, a feed comprising one or more suitable reactants is provided in step 24 and then is subjected to suitable treatment in step 26 to produce a gas mixture comprising CO and $H_2$. In some embodiments the feed in step 24 comprises methane and optionally ethane or ethanol. Any one or more of these reactants may be derived from renewable feedstocks such as corn, sugarcane, bagasse, sugar beets, potatoes, corn stover, municipal solid waste, other biomass sources, combinations of these, and the like. Techniques for converting the feed of step 24 into syngas in step 26 include steam reformation of natural gas or liquid hydrocarbons, gasification of coal or biomass. Catalytic partial oxidation has been used to convert biomass to syngas. Microwave energy has been used to split $CO_2$ into CO. The CO can then be combined with hydrogen to form syngas.

Concentrated solar power also is proposed to drive thermochemical reactions that split carbon dioxide to make CO.

Making syngas is exothermic and generates substantial amounts of heat. System 10 may use this heat for one or more purposes. For example, the heat can be transferred and used to convert ethanol to ethylene. The heat also can be used to distill propanol or to convert propanol to propylene.

The syngas prepared in step 26 and the partially purified ethylene feed mixture of step 18 are used as reactants in step 20 to carry out the hydroformylation of ethylene. An optional hydrogen rich stream 25 may be drawn off to be used elsewhere in system 10. Generally, the hydroformylation of ethylene produces a C3 product which is predominantly propionaldehyde and in some instances a small amount of 1-propanol. The reaction may be represented by the following reaction scheme (formation of the small amount of 1-propanol not shown):

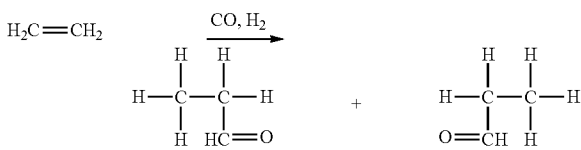

Schematically, hydroformylation converts the double bond into a single bond, adds H to one side of the new single bond, and C(O)H is added to the other side of the single bond. Two propionaldehyde products are shown because the H and carbonyl moiety can add across the formal double bond in two ways. In the case of ethylene, the two aldehyde products turn out to be the same structural compound. Thus, hydroformylation of ethylene yields a single C3 aldehyde product, namely propionaldehyde in this embodiment. Trace amounts of 1-propanol also tend to result, but the product is mostly propionaldehyde. For other linear olefins with more than two carbon atoms such as propylene or 1-butene, two different aldehyde compounds, isomers of each other, result.

Reacting ethylene with syngas using hydroformylation strategies is well-documented and described in detail in the patent and technical literature. Examples of literature that describes hydroformylation reactions include "New Syntheses with Carbon Monoxide", Ed. J. Falbe, Springer Verlag, New York, 1980, especially the Chapter "Hydroformylation, Oxo Synthesis, Roelen Reaction" by B. Cornils; U.S. Pat. Nos. 3,527,809, 3, 917,661; 4,148,830; 4,742,178, 4,769, 984; 4,885,401; 6,049,011; 8,552,240; and U.S. Patent Pub. No. 2205/0065389, each of which is incorporated herein by reference in its respective entirety for all purposes.

Hydroformylation is generally carried out using a suitable catalyst. A variety of suitable catalysts are discussed in the technical and patent literature cited herein. Because hydroformylation can produce at least two different products when using linear aliphatic olefins of 3 or more carbons, it has been the case that one of the products often is more desired than the other. Accordingly, conventional practice may balance catalyst activity against catalyst selectivity. A less active catalyst may be selected at the expense of activity in order to help ensure that the desired product is produced. However, selectivity is not a concern in the hydroformylation of ethylene. Regardless of how the H and C(O)H add across the C=C double bond of ethylene, the same aldehyde, namely, propionaldehyde and trace amounts of the corresponding alcohol 1-propanol, are produced. This means that highly active catalysts can be used to efficiently convert ethylene with high conversion to propionaldehyde and 1-propanol even though the feed mixture might contain other hydrocarbon (e.g., ethane or ethanol) constituents.

Using a highly active catalyst provides many advantages. Higher reaction rates and throughput can be obtained, increasing the production capacity of a facility per unit time. Syngas is used more efficiently, allowing lower volumes of syngas to be used. This makes the purge stream 44, described further below, easier to handle. Ethylene is converted to the desired C3 product(s) in higher yields.

A preferred class of highly active hydroformylation catalysts comprise rhodium in complex combination with CO and a triorgano phosphorous ligand. Examples of such ligands include trialkyl phosphites, tricycloalkyl phosphites, triaryl phosphites, triaryl phosphines, alkyl-diaryl-phosphines, bis-phosphite ligands, and combinations of these. Examples of rhodium catalysts including these ligands are further described in U.S. Pat. Nos. 3,527,809; 4,148,830; and 4,885,401. Each of these patents is incorporated herein by reference in its respective entirety for all purposes.

The amount of catalyst used to carry out hydroformylation may be selected within a wide range. In some modes of practice using catalysts comprising rhodium in complex combination with CO and a triorgano phosphorous ligand, the catalyst is used in a concentration such that (a) the molar P/Rh ratio is at least 2:1, (b) the total concentration of the coordinately active phosphorus is preferably at least 0.01 mol/l; and (c) the [P]/pco ratio maintained in the reactor is preferably at least 0.1 mmol/l/kPa, where [P] is the total concentration of the coordinately active phosphorus in the reaction medium, and Pco is the partial pressure of carbon monoxide in the gas phase. Desirably, the Rh concentration in the reaction mixture is in the range from $1 \times 10^{-5}$ to $1 \times 10^{-2}$ moles/liter or, in effect, in the range from 1 to 1000 ppm, preferably 20 to 500 ppm, based on the total weight of the reaction medium.

The hydroformylation reaction desirably is carried out in an oily solvent or a mixture of such solvents. Examples include aliphatic and aromatic hydrocarbons (e.g., heptanes, cyclohexane, toluene), esters (e.g., dioctyl phthalate), ethers, and polyethers (e.g., tetrahydrofuran, and tetraglyme), product aldehydes (e.g., propanal, butanal) the condensation products of the oxo product aldehydes or the triorganophosphorus ligand itself (e.g., triphenylphosphine). Alternatively, as described in U.S. Pat. Nos. 4,248,802, 4,808,756, 5, 312,951 and 5,347,045, which are all incorporated herein by reference, the catalyst may contain a hydrophilic group and an aqueous medium may be used.

Rhodium catalyst may be introduced into the reactor either as a pre-formed catalyst, for example, a solution of hydridocarbonyl tris(triphenylphosphine) rhodium(I) or the catalyst may be formed in situ. If the catalyst is formed in situ, the Rh may be introduced as a precursor such as acetylacetonatodicarbonyl rhodium(I) $\{Rh(CO)_2$ (acac)$\}$, rhodium oxide $\{Rh_2 O_3\}$, rhodium carbonyls $\{Rh_4 (CO)_{12}, Rh_6 (CO)_{16}\}$, tris(acetylacetonato) rhodium(I), $\{Rh(acac)_3\}$, or a triaryl phosphine-substituted rhodium carbonyl $\{Rh (CO)_2 (PAr_3)\}_2$, wherein Ar is an aryl group and acac is acetylacetone.

Hydroformylation can be carried out at one or more temperatures selected from a wide range. In some embodiments, suitable temperature(s) are in the range from 50° C. to 200° C., desirably from 60° C. to 150° C. and more desirably from 70° C. to 120° C.

The hydroformylation reaction in many suitable embodiments is conducted at a low pressure, e.g., a pressure in the range of 0.05 to 50 MPa (absolute), and preferably in the range of about 0.1 MPa to 30 MPa, most preferably at a pressure below 5 MPa. Desirably, the partial pressure of carbon monoxide is not greater than 50% of the total pressure.

The proportions of carbon monoxide, hydrogen, and ethylene in the hydroformylation reaction medium can be selected within a wide range. In some embodiments, based on the total amount of CO, hydrogen, and ethylene, CO is from about 1 to 50 mol %, preferably about 1 to 35 mol %; $H_2$ is from about 1 to 98 mol %, preferably about 10 to 90 mol %; and ethylene is from about 0.1 to 35 mol %, preferably about 1 to 35 mol %. It will be appreciated that if the partially purified ethylene feed mixture itself contains carbon monoxide and/or hydrogen, the proportions of syngas supplied to step 20 may be adjusted accordingly to achieve the desired proportions in the reactor.

In many modes of practice, the hydroformylation reaction of step 20 desirably takes place in the presence of both liquid and gas phases. The reactants generally are in the gas phase. Catalyst typically is in the liquid phase. Because the reactants are gaseous compounds, a high contact surface area between the gas and liquid phases is desirable to enhance good mass transfer. A high contact surface area between the catalyst solution and the gas phase may be provided in any suitable manner. In a batch process, the batch contents are thoroughly mixed during the course of the reaction. (in some cases the liquid phase is sprayed through nozzle to increase contact surface area) In a continuous operation the reactor feed gas can be contacted with the catalyst solution in, for example, a continuous-flow stirred autoclave where the gas is introduced and dispersed at the bottom of the vessel, preferably through a perforated inlet (e.g., a sparger). Good contact between the catalyst and the gas feed may also be provided by dispersing the solution of the Rh catalyst on a high surface area support, a technique well known in the art as supported liquid phase catalysis, or providing the Rh as part of a permeable gel.

The reaction may be conducted either in a batch mode or, preferably, on a continuous basis. One or more reactors may be used in continuous modes to carry out the reaction in one or more stages. When a single reactor is used, a suitable liquid product volume residence time is 1 hour$^1$ to 10 hour$^1$, preferably 2 hour$^1$ to 8 hour$^1$, more preferably 3 hour$^1$ to 6 hour$^1$. If a plurality of reactors is used in series, a liquid product volume space velocity in each reactor independently may be in the range from 1 hour$^{1}$ to 20 hour$^{1}$, preferably 2 hour$^{-1}$ to 15 hour$^{1}$.

Suitable reactor schemes are disclosed, for example, in Harris et al in U.S. Pat. Nos. 4,287,369 and 4,287,370 (Davy/UCC), Tsonuda et al in U.S. Pat. No. 4,322,564 (Mitsubishi), Fischer et al in U.S. Pat. No. 4,479,012, Kummer et al in EP-A-114,611 (both BASF), Cornils et al in EP-A-103,810, Kalbfell et al in EP-A-144,745 (both Hoechst/Ruhrchemie). Optionally two or more reactor vessels or reactor schemes may be configured in parallel. In other modes of practice, hydroformylation is carried out in two or more vessels in series. Suitable reactor configurations are disclosed, for example, by Fowler et al in British Patent Specification No. 1,387,657, by Bunning et al in U.S. Pat. No. 4,593,127, by Miyazawa et al in U.S. Pat. No. 5,105,018, and by Unruh et al in U.S. Pat. No. 5,367,106. The individual hydroformylation reactors may be of the standard types as described by Denbigh and Turner in "Chemical Reactor Theory" ISBN 0 521 07971 3, by Perry et al in "Chemical Engineers' Handbook" ISBN 0-07-085547-1 or any more recent editions, e.g., a continuous stirred tank or a plug flow reactor with adequate contact of the gas and the liquid flowing through the reactor. Advantageously these plug flow reactor designs or configurations include ways of partial back-mixing of the reactor product liquid, as explained, for example, by Elliehausen et al in EP-A-3,985 and in DE 3,220,858).

In a single reactor stage, reactor size may be minimized by carrying out the reaction at high temperatures (>130° C.). Higher temperatures, however, may tend to degrade the catalyst. In a preferred embodiment, therefore, hydroformylation is carried out in different reaction zones. These zones may be different reaction vessels or zones in a single reaction vessel with physically different reaction conditions. An example of a single vessel with different reaction zones is a plug flow reactor in which the temperature increases with travel downstream along the length of the plug flow reactor. By appropriately utilizing different reaction zones or stages, high conversion hydroformylation of ethylene may be achieved with minimum reactor volume and maximum catalyst stability. In a preferred embodiment, two or more reactors are used in series. When two reactors are used, they are advantageously staged such that additional ethylene conversion results. The reactors used may be two sequential, well-stirred tank reactors in which the gaseous dilute ethylene is contacted with a liquid phase that contains the Rh catalyst. A second or downstream stage reactor desirably may use the same or, alternatively, a higher activity catalyst or higher catalyst concentration than a first stage or upstream stage.

In a preferred embodiment the reactors are staged such that more than 70% of the ethylene is converted in a first reactor and more than 70% of the remaining ethylene is converted in a second reactor. This gives an overall ethylene conversion in excess of 91%. Another configuration of two reactors that may be used to obtain high conversion from a dilute ethylene feed is a well-stirred tank reactor followed by a plug flow reactor.

The hydroformylation reaction of step 20 converts ethylene to C3 products at high yield. In many modes of practice, at least 80 weight %, preferably 90 weight %, most preferably 95 weight %, and even substantially all of the ethylene is converted to one or more C3 products. The major, and preferred, product of ethylene hydroformylation carried out in accordance with step 20 is propionaldehyde (also referred to as 1-propanal). Trace amounts of 1-propanol also are produced as an additional C3 product. The 1-propanal has utility as an intermediate in the manufacture of numerous commercially important chemicals, and the invention also provides processes in which hydroformylation is followed by reactions producing such chemicals.

Hydroformylation according to step 20 generally produces a product mixture comprising the desired C3 product(s) as well as additional ingredients including remaining solvent, catalyst, ethane, ethanol, hydrogen, and CO. It is desirable to carry out step 40 in order to separate the C3 products from the remaining gases. This separation can be accomplished in a variety of ways. For example, the product mixture can be treated to provide a gas phase purge stream 45 and a liquid stream 42. The purge stream 45 tends to include a major amount of the ethane, hydrogen, and CO in the product mixture resulting from step 20. The liquid stream 42 tends to include a major amount of the solvent, catalyst, and C3 products in the product mixture resulting from step 20. A major amount means that the stream comprises more than 50 weight percent, preferably more than 75 weight percent, and more preferably more than 90 weight percent of a constituent based on the total weight of the constituent present in the product mixture resulting from step 20.

The liquid stream 42 is treated in step 44 in order to isolate the C3 products such as propionaldehyde. This can be accomplished in a variety of ways. According to one approach, the propionaldehyde can be distilled from the liquid stream. This provides a first liquid stream comprising a major amount of the C3 products and a second liquid stream comprising catalyst and solvent. The first liquid stream may be recovered for storage or further handling. The second liquid stream optionally may be recycled (not shown) back to step 20 for further hydroformylation.

Separation in step 40 also produces a purge stream 45 comprising a major amount of the ethane, $H_2$, and CO in the product mixture resulting from step 20. Carbon dioxide and other compounds also may be present. Optionally, purge stream 45 may be treated to remove the carbon dioxide and other compounds, if any. Advantageously, because of partial purification carried out in step 20, the overall volume of the purge stream 45 is relatively lower compared to the volume that would result in the absence of partial purification. As a consequence, the purge stream 45 is more readily recycled back to step 16. This allows ethane in the purge stream 44 to be recycled as a reactant to make more ethylene. According to conventional practices, oxygen also is included in the feed used to make syngas. The CO and hydrogen also end up being recycled back to step 20 after steps 16 and 18 are carried out. If desired the syngas (CO+ hydrogen) and hydrocarbon portions of stream 45 optionally can be separated for optimum recycle. Ethane, which is a relatively expensive reactant, is thereby used with greater utilization as compared to a process without such recycle. Higher conversion of ethane to ethylene also is achieved. The recycled CO and hydrogen also are used with higher utilization and efficiency.

Figure 2:
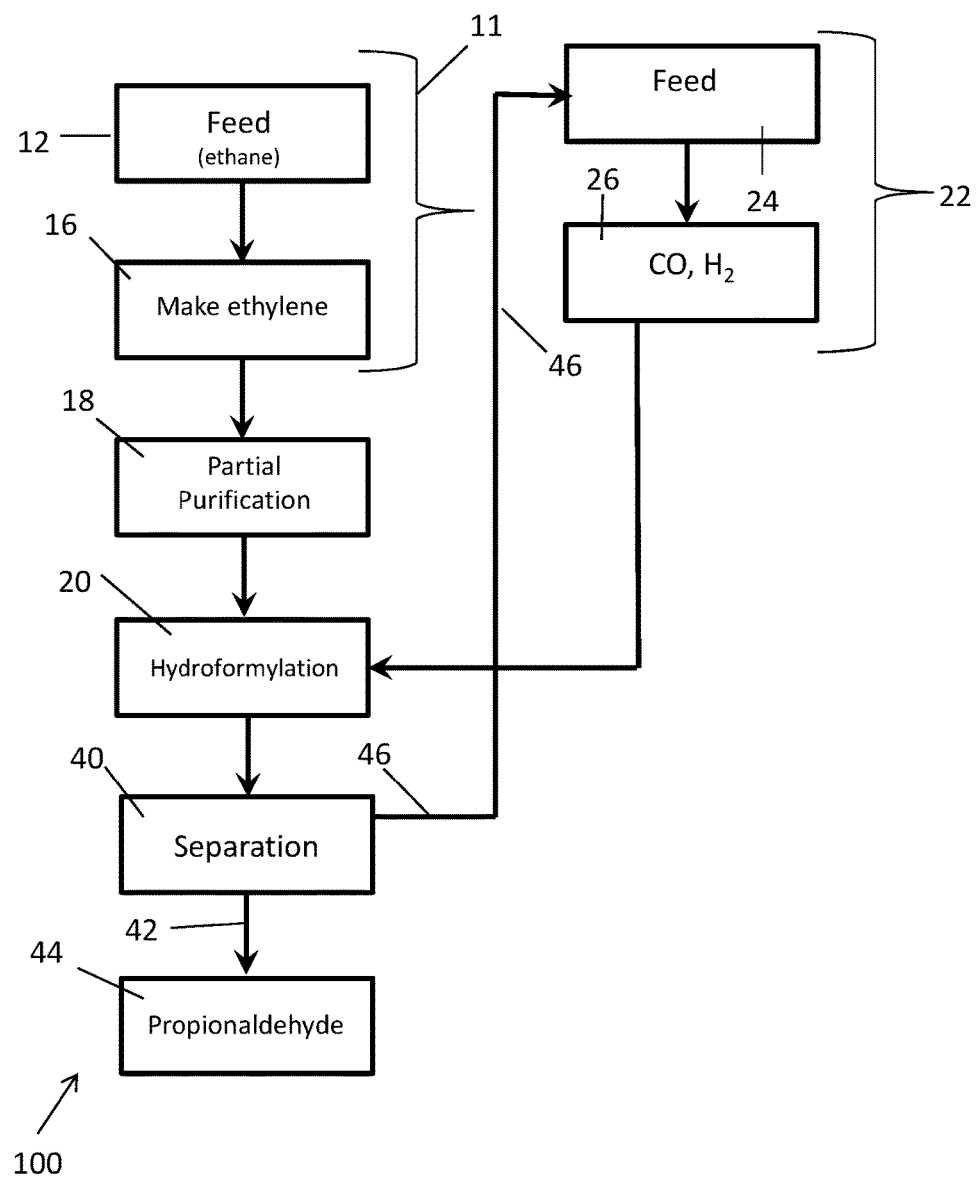
FIG. 2 schematically shows a flow chart of another embodiment of a process of the present invention.

FIG. 2 shows an alternative embodiment of a process 100 according to the present invention. Process 100 is similar to process 10 of FIG. 1 except that process 100 does not include purge stream 45 being recycled back to step 16. Instead, the purge materials (e.g., ethane, hydrogen, CO) are taken from step 40 as purge stream 46. Purge stream 46 is fed as a recycle stream back to step 24, where at least a portion of the constituents of purge stream 46 are used as a feed to make syngas in step 26. An advantage of carrying out partial purification in step 18 is that the relative total amount of ethane is sufficiently low in the product mixture resulting from step 20 such that purge stream 46 can be recycled back to make more syngas without adverse result. The amount of ethane in purge stream 46 is sufficiently low relative to the syngas needed so that this stream can be readily mixed with methane to make more syngas. Otherwise, if the amount purge stream ethane 46 were too high, then recycling the purge stream 46 to make more syngas would be problematic. This is due to the fact that ethane oxidation is more exothermic than methane oxidation. When the reaction is too exothermic, the combustion temperatures may be high enough to lead to lower syngas production rates than might be desired. Purge stream 46 allows the ethane, hydrogen and CO to be used with higher utilization and efficiency via recycle as compared to a scenario in which the contents of purge stream 46 were to be discarded or burned as fuel. In particular, ethane utilization is greatly increased, which is technically and economically significant.

Optionally, a preferred mode of practice involves separating (not shown) purge stream 46 an ethane rich faction and a hydrogen/CO rich fraction allowing dual recycle. The ethane rich fraction can be recycled back to step 16 to make more ethylene directly or via step 12. The hydrogen and CO rich fraction with the reduced ethane content can be recycled to step 20 or used more easily for syngas production. For example, purge stream 46 might include 25 weight percent ethane based on the total weight of the purge stream. Fractionation or other separation technique can be used to prepare a CO and hydrogen rich stream containing 5 weight percent or less ethane. Reducing the ethane content for syngas production is very helpful in order to allow the recycle to be used for syngas production more easily.

Figure 3:
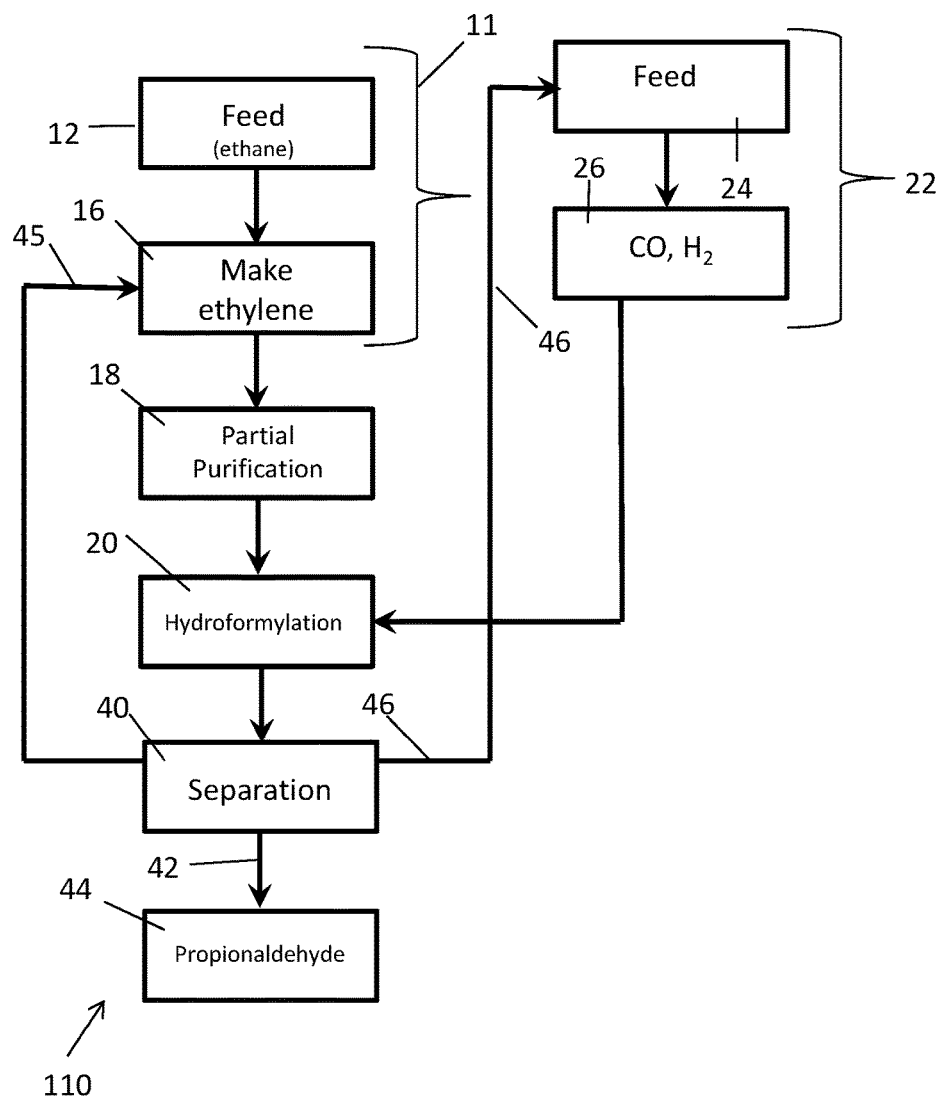
FIG. 3 schematically shows a flow chart of another embodiment of a process of the present invention.

FIG. 3 shows another embodiment of a process 110 according to the present invention. Process 110 is a combination of the processes shown in FIGS. 1 and 2. Process 100 provides and recycles both purge stream 45 in a manner similar to FIG. 1 as well as purge stream 46 in a manner similar to FIG. 2. In particular, by-product hydrogen can be used for propionaldehyde reduction and/or to improve syngas production efficiency.

Figure 4:
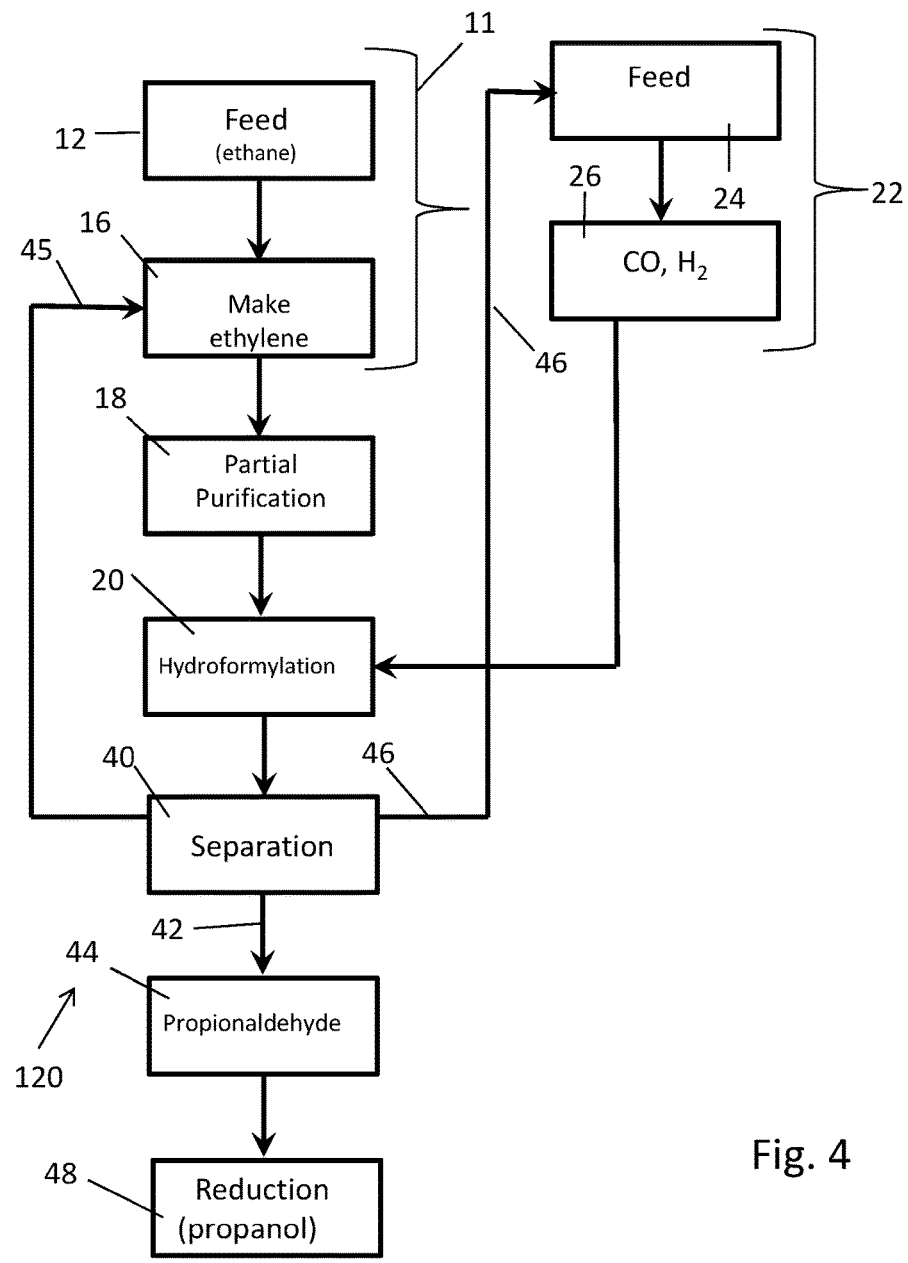
FIG. 4 schematically shows a flow chart of another embodiment of a process of the present invention.

The propionaldehyde produced in the processes shown in FIGS. 1, 2 and 3 is a useful product with many uses. As one use, propionaldehyde can be used as a reactant to make 1-propanol. Accordingly, FIG. 4 shows an alternative embodiment of a process 120 of the present invention whose practice produces 1-propanol. Process 120 is similar to process 110 of FIG. 3 except that process 120 includes the further step 48 in which propionaldehyde is converted into propanol. According to one illustrative approach for carrying out step 48, the propionaldehyde is reduced to prepare 1-propanol in high yield in the presence of a suitable reducing agent and optionally a suitable catalyst. In one mode of practice, the reducing agent is hydrogen, and the reaction system is a gas or liquid phase hydrogenation reaction system.

The hydrogen for process step 48 can be optionally and advantageously obtained from that produced in step 18 or step 26. The reaction scheme may be represented by the following:

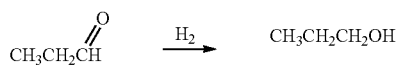

Reaction conditions and process for converting propionaldehyde to 1-propanol according to this reaction are well known and have been described in Kirk-Othmer Encyclopedia of Chemical Technology $3^{rd}$ Edition Volume 16 page 637.

The propionaldehyde also can be used in other processes including the manufacture of propanoic acid, wherein the propanal is oxidized; a process for the manufacture of an aldol dimer or trimer, wherein the propanal is self-aldolized; a process for the manufacture of a saturated aldehyde, wherein the aldol dimer or trimer is hydrogenated to a corresponding saturated aldehyde; a process for the manufacture of an unsaturated alcohol, wherein the aldol dimer or trimer is selectively hydrogenated; a process for the manufacture of a saturated alcohol, wherein all double bonds in the aldol dimer or trimer are hydrogenated; a process for the manufacture of a saturated alcohol or acid, wherein the saturated aldehyde produced by hydrogenation of the aldol dimer or trimer is hydrogenated or oxidized to form the corresponding saturated alcohol or acid; a process for the manufacture of trimethylol ethane, wherein propanal is condensed with formaldehyde to form the trimethylol ethane; a process for the manufacture of a multi-methylol alkane or alkene, wherein the aldol dimer or trimer and/or the saturated aldehyde produced therefrom is aldol-condensed with formaldehyde to form the corresponding multi-methylol alkane or alkene, a process for the manufacture of an ester, wherein the saturated alcohol or the acid is esterified; a process for the manufacture of an aldol tetramer or pentamer, or mixtures thereof, by aldolization of the propanal or aldehyde mixture from hydroformylation; a process for the manufacture of a C12 to C20 alcohol or alcohol mixtures, wherein the aldol tetramer, pentamer, or mixture, is hydrogenated to the corresponding alcohol or alcohol mixture; a process for the manufacture of liquid olefin or olefin mixture, wherein the tetramer or pentamer alcohol is dehydrated; and a process for the manufacture of a liquid paraffin or paraffin mixtures, wherein the olefin or olefin mixture is hydrogenated.

Figure 5:
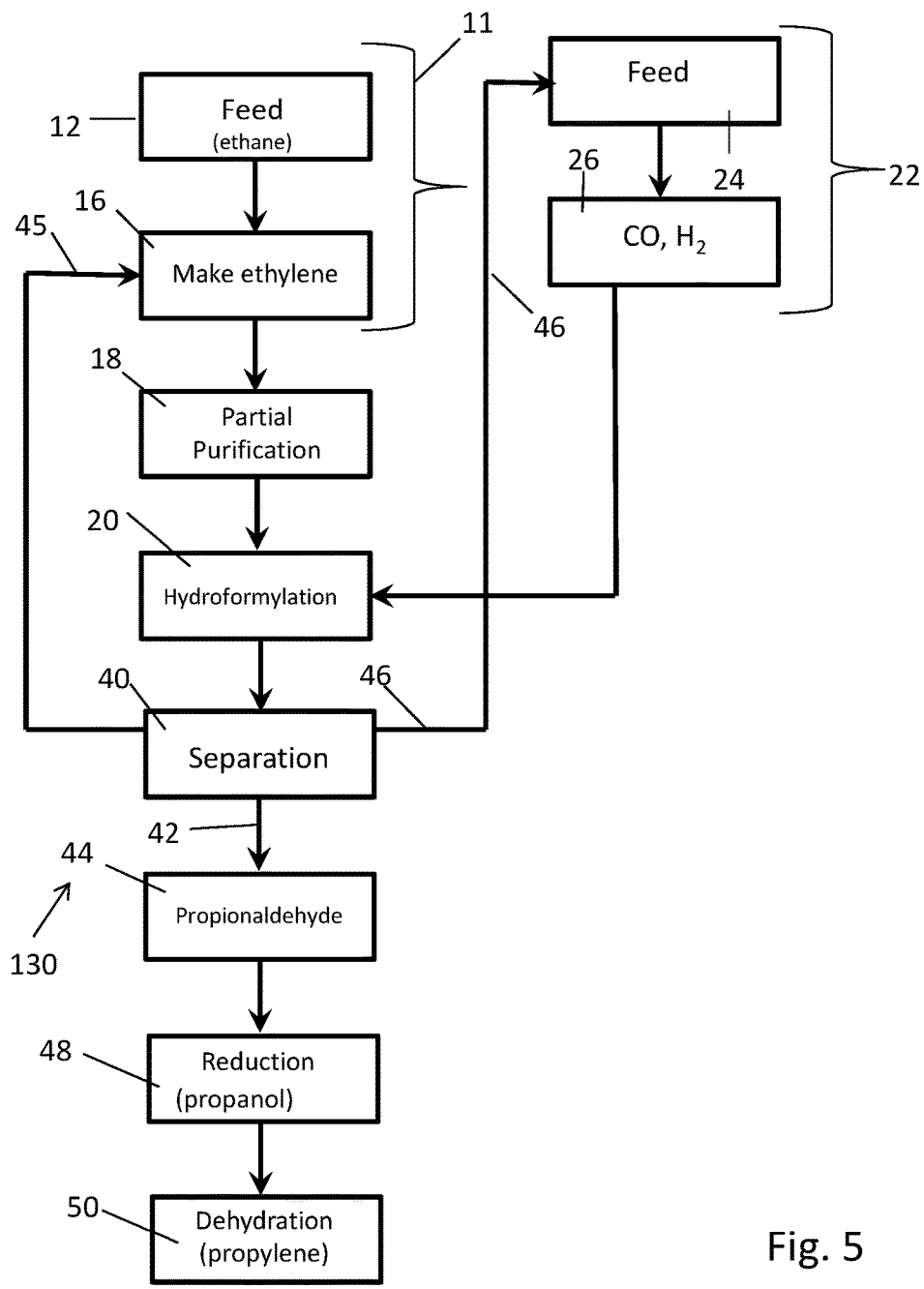
FIG. 5 schematically shows a flow chart of another embodiment of a process of the present invention.

The 1-propanol produced in process 120 according to FIG. 4 also is a useful product with many uses. As one use, 1-propanol can be used as a reactant to make the commercially important propylene, an olefin with strong commercial demand. Accordingly, FIG. 5 shows an alternative embodiment of a process 130 of the present invention whose practice produces propylene. Process 130 is similar to process 120 of FIG. 4 except that process 130 further includes the further step 50 in which 1-propanol is converted into propylene. According to one illustrative approach for carrying out step 50, the 1-propanol of step 48 optionally is purified and then introduced to a liquid or gas phase dehydration reaction system. The reaction scheme may be represented by the following:

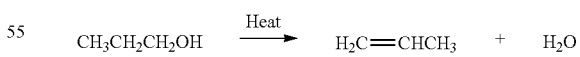

Reaction conditions and processes for converting 1-propanol into propylene using one or more catalysts are well known and have been widely described in the literature. Many catalysts can be used. Alumina is one example. See, for example, U.S. Pat. No. 5,475,183 and U.S. Pat. No. 8,552,240. The resultant propylene optionally may be purified and then packaged, stored, converted to other products, or otherwise handled as desired.

Figure 6:
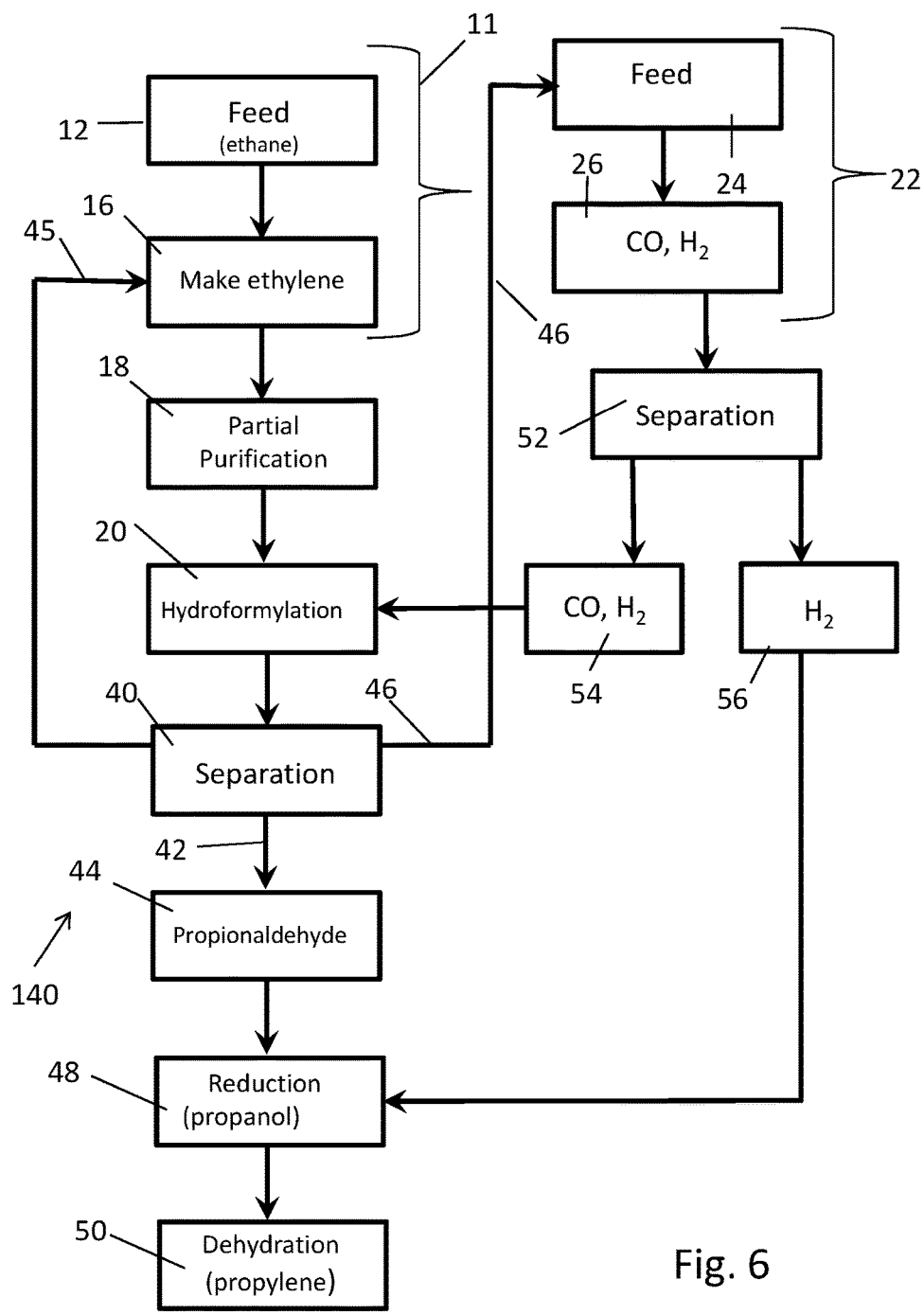
FIG. 6 schematically shows a flow chart of another embodiment of a process of the present invention.

FIG. 6 shows an alternative embodiment of a process 140 that uses the syngas prepared in step 26 for multiple purposes. Process 140 is similar to process 130 of FIG. 5 except that process 140 includes the additional separation step 52 in which the syngas prepared in step 26 is separated into two streams. A first stream 54 includes CO and hydrogen that is supplied to the hydroformylation reaction of step 20. A second stream 56 comprises hydrogen that is fed to step 48 to be used as a reducing agent to help reduce propionaldehyde to 1-propanol.

Figure 7:
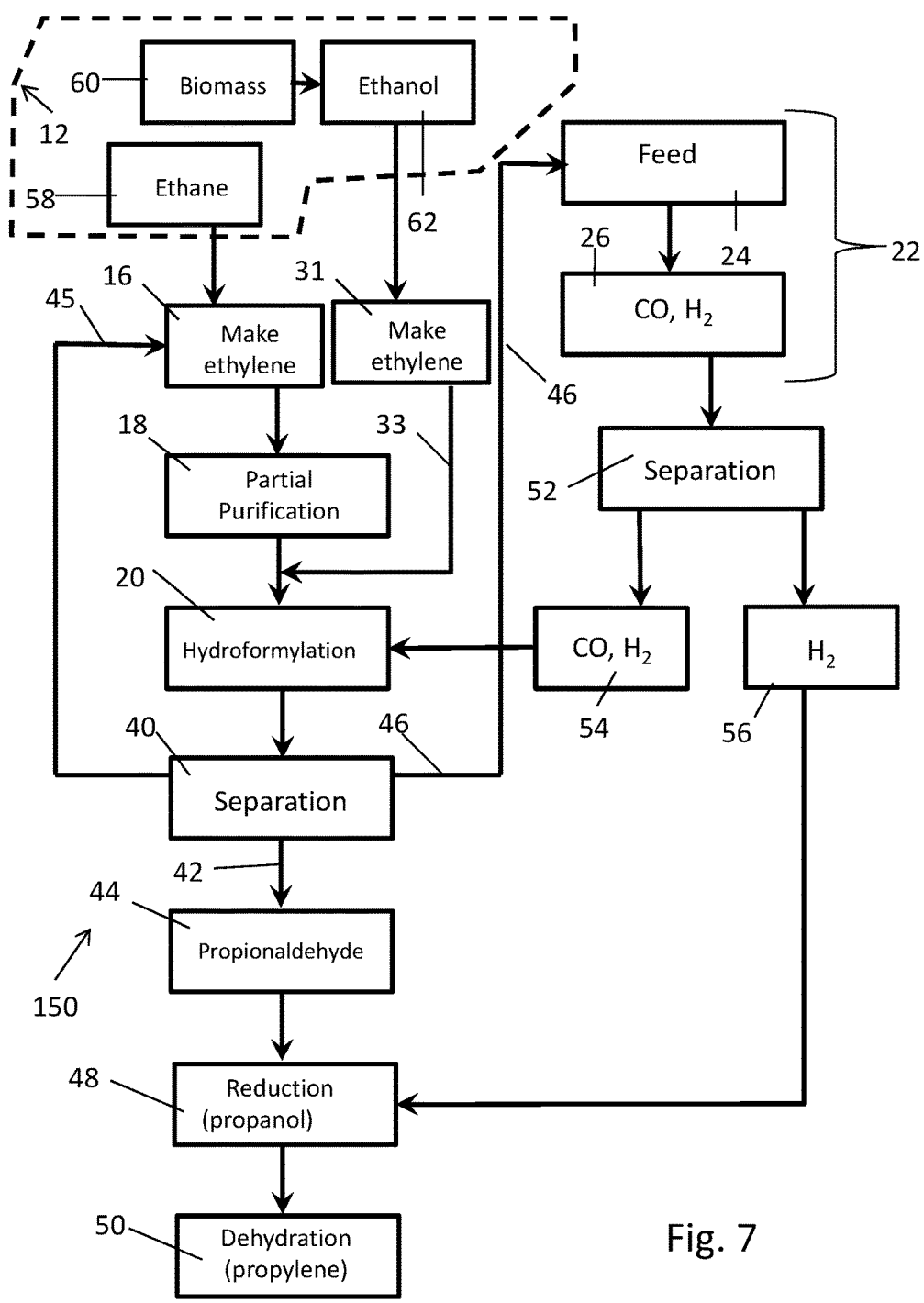
FIG. 7 schematically shows a flow chart of another embodiment of a process of the present invention.

FIG. 7 shows another embodiment of a process 150 of the present invention. Process 150 shows one option for practicing process 140 of FIG. 6. According to process 150, feed 12 is derived from both an ethane source 58 as well as from renewable feedstocks in the form of biomass source 60. Examples of biomass sources include corn, sugarcane, sugar beets, potatoes, bagasse, corn stover, municipal solid waste, combinations of these, and the like. Biomass source 60 is converted into ethanol in step 60.

Ethane provided in step 58 and ethanol provided in step 62 are then converted into ethylene in steps 16 and 31, respectively. Each of ethane and ethanol is converted into ethylene using different reaction strategies. As described above, steam cracking is one strategy by which ethane is converted into a mixture comprising unreacted ethane and up to 75 weight percent of ethylene based on the total weight of hydrocarbons in the resultant product mixture. In contrast, ethanol is much more readily converted into ethylene at substantially 100% conversion efficiency using processes as described in U.S. Pat. No. 8,426,664; U.S. Pat. No. 8,389,784; U.S. Pat. No. 8,273,930; U.S. Pat. No. 4,873,392; U.S. Pat. No. 4,847,223; U.S. Pat. No. 4,727,214; U.S. Pat. No. 4,670,620; U.S. Pat. No. 4,423,270; and U.S. Pat. No. 4,302,357. Accordingly, in steps 16 and 31, respectively, each of the ethane and ethanol feeds 58 and 62 is independently converted into ethylene. Both streams may be independently purified to remove higher hydrocarbons, catalyst poisons, etc. Partial purification according to step 18 is practiced with respect to the ethylene stream derived from ethane via step 16 inasmuch as ethanol is converted to ethylene in step 31 in such high yield that removing a portion of the remaining ethanol is unnecessary. The separate streams can then be combined or independently provided to the hydroformylation reaction of step 20. For example, the ethylene rich stream 33 is combined with the ethylene rich stream obtained from partial purification, and the combination is fed to the hydroformylation step 20.

Figure 8:
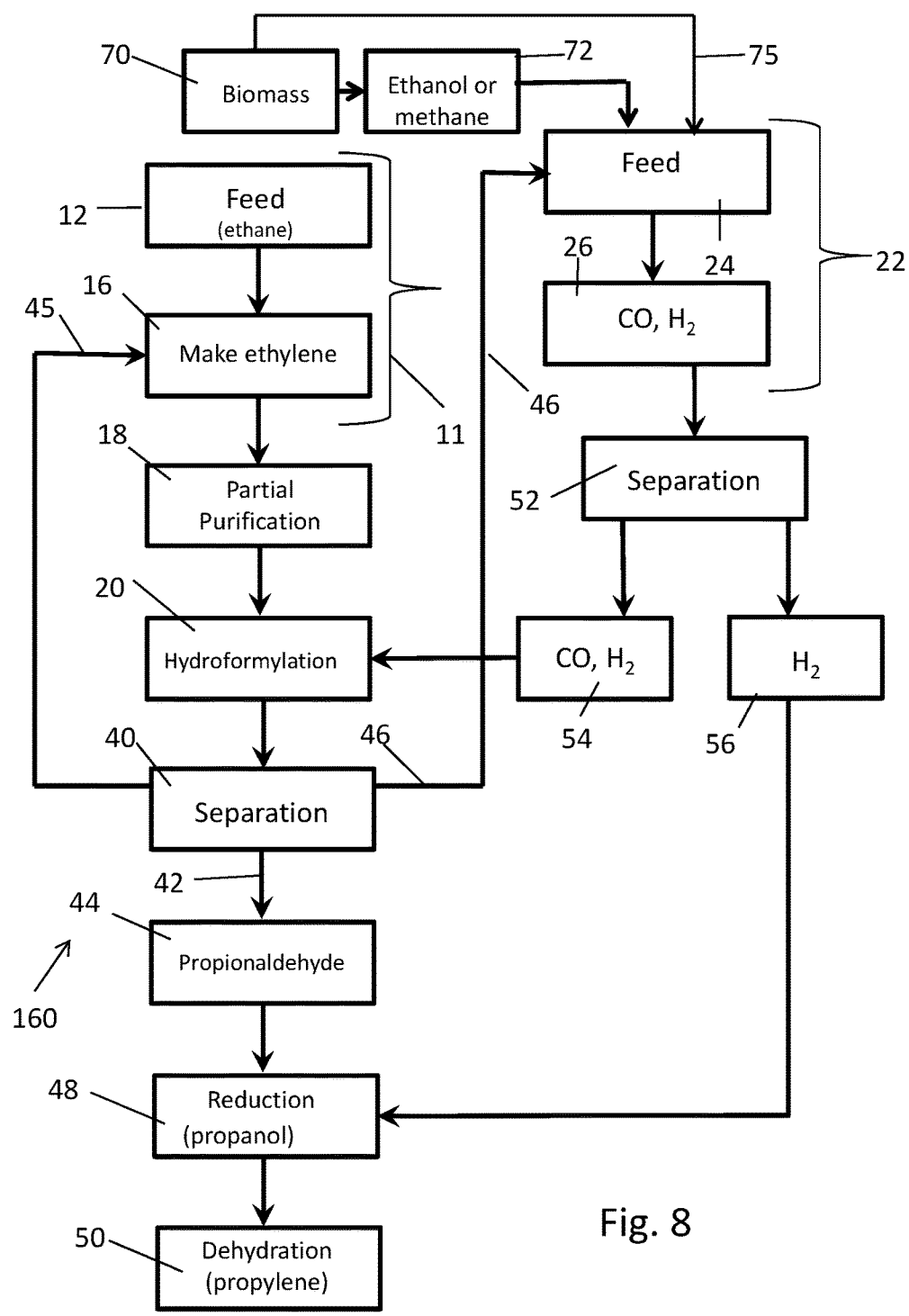
FIG. 8 schematically shows a flow chart of another embodiment of a process of the present invention.

FIG. 8 shows another embodiment of a process 160 according to the present invention. Process 160 shows another option for practicing process 140 of FIG. 6. Process 160 shows that the feed provided in step 24 can be derived at least in part from biomass. In step 70, renewable feedstock from a suitable biomass is provided. Examples of such biomass include corn, sugarcane, sugar beets, potatoes, bagasse, corn stover, municipal solid waste, combinations of these, and the like. In step 72, the biomass is converted into methane and/or ethanol. The methane and/or ethanol is then used as at least a portion of the feed provided in step 24. As an alternative to step 72, or in combination with step 72, biomass 70 may be directly supplied via stream 75 to step 24 in order to use the biomass to make CO and hydrogen. Like process 150 of FIG. 7, process 160 shows another way to make propylene from renewable resources.

Figure 9:
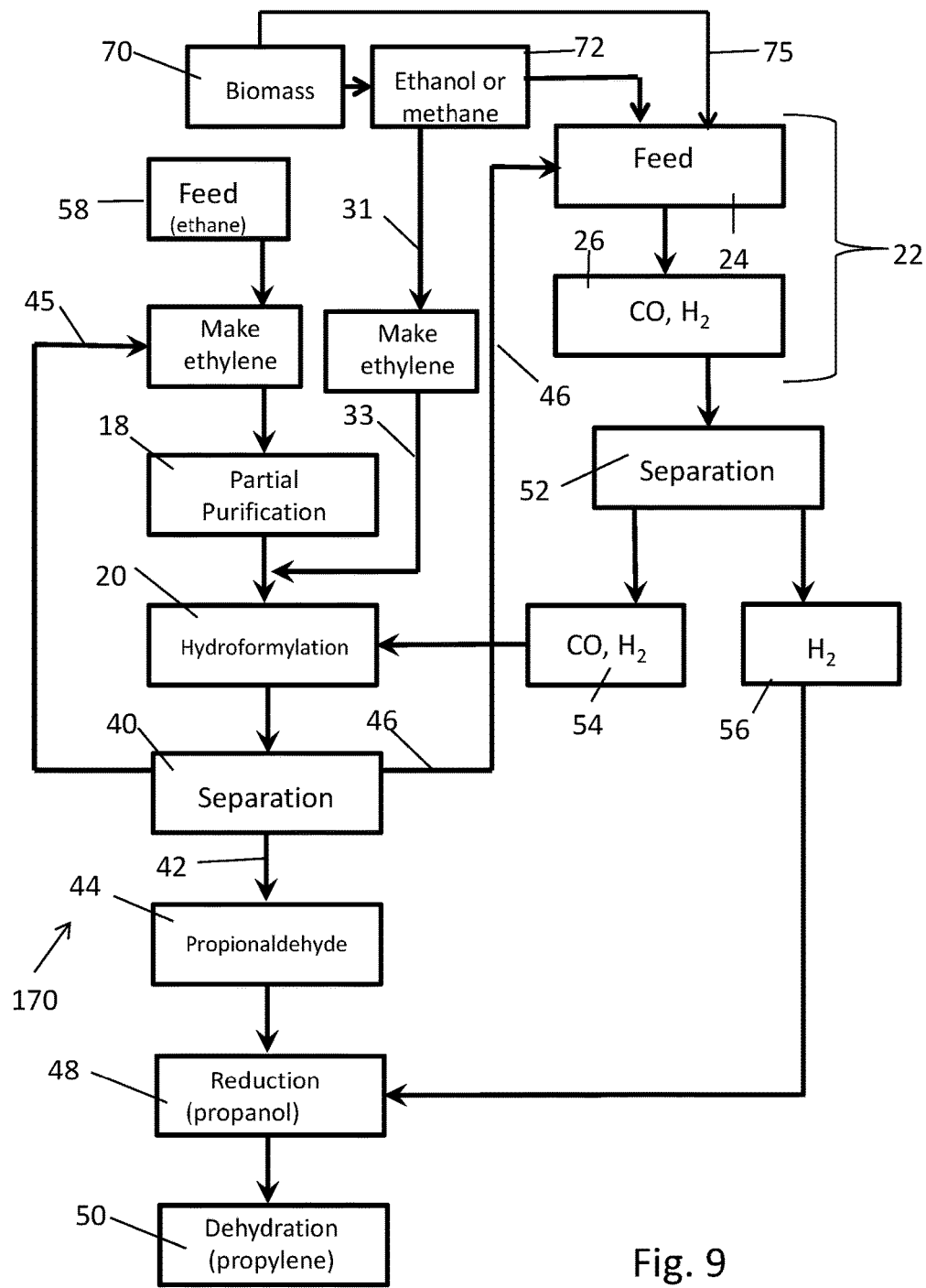
FIG. 9 schematically shows a flow chart of another embodiment of a process of the present invention.
Figure 10:
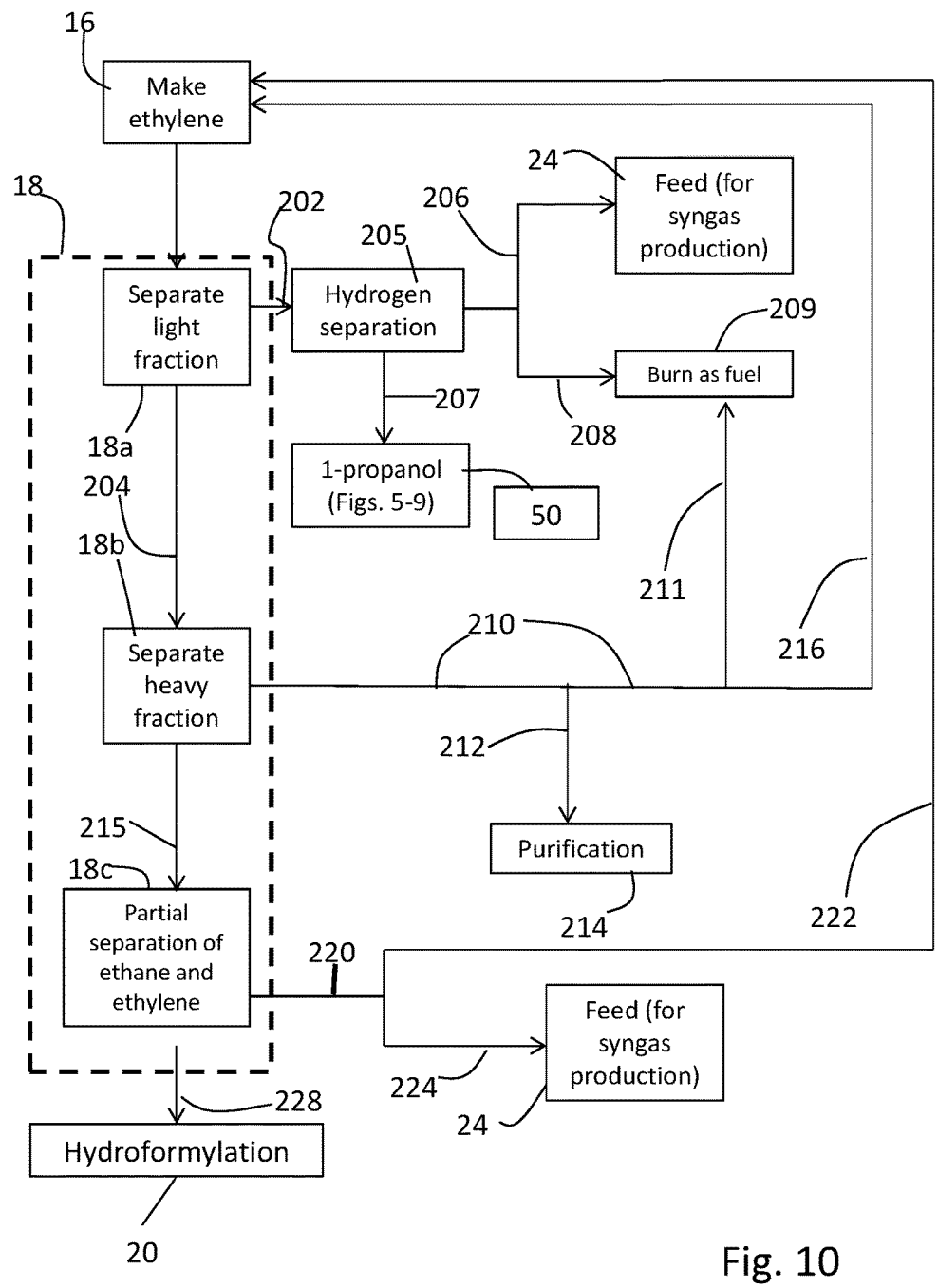
FIG. 10 shows an embodiment of a partial purification strategy useful in the practice of the present invention, including in the practice of any of the process embodiments described in FIGS. 1-9.

FIG. 9 shows another embodiment of a process 170 according to the present invention. Process 170 combines features of FIGS. 7 and 8 in that the ethanol produced in step 72 is not only used as all or a portion of the feed in step 24 but also to make ethylene in step 31, which is then supplied to carry out hydroformylation in step 20. In this way, both the ethylene and syngas used to make the C3 products are derived from renewable resources. Process 170 may be used, if desired, to prepare polypropylene in which all of the reactants are sourced from biomass.

The present invention will now be further described with reference to the following illustrative examples.

Example 1

Synthesis gas is produced from natural gas by existing processes well known in the art having a hydrogen to carbon monoxide mole ratio in the 1:1 to 3:1 range, preferably ~2:1. Excess hydrogen is removed from the synthesis gas by existing processes to reduce the hydrogen to carbon monoxide ratio to about 1.03:1. The resulting synthesis gas is reacted with an enriched, partially purified ethylene product stream containing at least some (~18%) ethane using a complex rhodium in complex combination with carbon monoxide and Triphenyl Phosphine containing catalyst system at 60° C. to 140° C. range to produce propionaldehyde and some propanol. (U.S. Pat. No. 3,527,809 & U.S. Pat. No. 4,148,830). The ethylene conversion is >90% of the contained ethylene. The condensed propionaldehyde and propanol, which is separated from ethane and any other gases, are further hydrogenated under pressure using in part the excess hydrogen removed above to produce propanol. The propanol is optionally purified for sale or dehydrated in a subsequent reactor to produce propylene by liquid or gas phase process well known in the art. The unreacted ethane stream and other gases which may contain at least some ethylene may optionally subjected to purification, burned as fuel, fed to the synthesis gas unit or recycled to ethylene production.

Example 2

In this example, a stream containing 85% ethylene, ~14% ethane and 1% hydrogen are fed together with 1.04:1 $H_2/CO$ syngas to a staged commercially typical liquid phase hydroformylation reaction system containing propionaldehyde with a complex rhodium in complex combination with carbon monoxide and Triphenyl Phosphine containing catalyst system at 60° C. to 140° C. range to produce propionaldehyde and some propanol. The crude liquid product stream is separated from the gas stream. Propionaldehyde is distilled from the concentrated catalyst stream and hydrogenated as is in the liquid and/or gas phases using catalysts typical to those known in the art to produce propanol. Propanol is separated from ethane other gases, purified for sale and/or subjected to dehydration to produce propylene. Ethane as well as other gases are optionally purified for recycle, burned as fuel and or fed to the synthesis gas unit. Ethylene conversion exceeds 80% of theoretical after the $1^{st}$ stage and exceeds 95% of the theoretical after the $2^{nd}$ stage. The $2^{nd}$ stage may utilize a higher catalyst concentration then the $1^{st}$ stage as desired.

Example 3

In this example crude ethylene is produced in total or in part via dehydration of ethanol produced from bio-mass. Syngas ($H_2/CO$ 2:1) is also optionally produced in part or total from biomass through gasification or through reforming of methane or partial oxidation produced from biomass through biodegradation. Carbon dioxide and other acidic by-products are optionally removed from the synthesis gas using the carbon dioxide removal system. The resulting relatively pure ethylene feed stream containing >95% ethylene based on total carbon content, is co mixed with synthesis gas having a hydrogen to carbon monoxide mole ratio of ~1.03:1 and subjected to the hydro-formylation reaction system using a catalyst system as described in U.S. Pat. No. 3,527,809 or U.S. Pat. No. 4,885,401 dissolved in propionaldehyde under pressure and at a temperature of 75° C. to 125° C. Over 98% of the contained ethylene is converted to produce a mixture of propionaldehyde and some propanol employing a multi-staged reaction system. Any unreacted ethylene together with any other hydrocarbon and or gases are separated from the propionaldehyde and propanol byproduct. The gaseous fraction may be subjected to purification and use or optionally recycled to syngas production. The condensed propionaldehyde and propanol is further hydrogenated under pressure (using hydrogen from the syngas unit) to propanol. The propanol is dehydrated in either the gas phase or in an aqueous acidic phase in a subsequent reactor to produce propylene. This mode demonstrates production of propylene from biomass and using a highly active phosphite ligand catalyst system. Catalyst is recycled as described in U.S. Pat. No. 4,148,830.

Example 4

In this example 1-propanol is produced by one of preferred modes 1, 2 or 3. A portion of the propanol is purified for sale. The remaining 1-propanol is subjected to dehydration, either liquid or gas phase to produce propylene. Alternatively the liquid propanol is stored for later conversion to propylene as desired. The propylene is purified for sale or used to produce propylene oligomers, polypropylene or propylene based polymers. Any by-product streams may be optionally recycled to dehydration and/or fed to the synthesis gas unit. This mode demonstrates co-production of propanol and propylene.

Example 5

A single or multi-staged commercially typical hydroformylation reaction system is charged with propionaldehyde, Rhodium catalyst carbon monoxide complex and tris(2,4-ditert-butyl phenyl) phosphite ligand. The system is brought to an appropriate temperature and pressure such that propionaldehyde remains predominately in the liquid phase. In this example, an ethane gas cycle stream containing ~97% ethylene together with some ethane and/or some hydrogen are fed together with 1.04:1 $H_2/CO$ syngas continuously. The reaction temperature and feed rates are controlled such that conversion of the contained ethylene to propionaldehyde exceeds 95% of that fed. Both liquid and a gas stream are removed continuously from the reaction system. The liquid phase is flashed at lower pressure to remove the bulk of the product propionaldehyde. A portion of the propionaldehyde containing the catalyst are recycled to the reactor. Ethane is condensed from the gas phases and recycled back to the ethane reaction system. The uncondensed synthesis gas is recycled back to the hydroformylation reactor. The crude product stream may be partially purified from ethane or hydrogenated as is in the liquid and/or gas phases using catalysts typical to those known in the art to produce propanol. Propanol is separated, purified for sale and/or subjected to dehydration to produce propylene. Purge streams may be optionally fed to the synthesis gas reaction system. Ethylene conversion exceeds 95% of that contained in the feed.

Example 6

This example describes a simulation in which high purity ethylene (99.89% by weight ethylene, stream 2) is prepared from a crude ethylene stream (stream 1). According to the simulation, a crude feed comprising 70 weight percent ethylene and 30 weight percent ethane, collectively referred to as the "Crude C2" feed is feed in stream 1 to a distillation column. The Crude C2 feed is provided at a mass flow rate of 125,000 pounds/hr, a temperature of −5° F., and a pressure of 450 psia. Purified ethylene is recovered in stream 2 at 87584 pounds/hr at a temperature of −7.8° F. at a pressure of 350 psia. The purified ethylene stream includes 99.9 weight percent ethylene and 0.10 weight percent ethane. Purified ethane is recovered as stream 3 at 37,416 pounds per hour, a temperature of 31.7° F., and a pressure of 350 psia. The purified ethane stream includes 0.02 weight percent ethylene and 99.98 weight percent ethane.

To accomplish this degree of purification at the simulated flow rates, the simulation indicates that a distillation tower is needed with a 13 foot diameter, a height of 216 feet, a reflux ratio of 4.3, and a refrigeration duty of 48.4 MM btu/hr. These results show that producing highly pure ethylene from the Crude C2 feed requires relatively large amounts of energy using a relatively large distillation column.

Example 7

This example describes a simulation in which partially purified ethylene (90.2% by weight ethylene, stream 2) is prepared from a crude ethylene stream (stream 1). According to the simulation, a crude feed comprising 70 weight percent ethylene and 30 weight percent ethane collectively referred to as the "Crude C2" feed is feed in stream 1 to a distillation column. The Crude C2 feed is provided at a mass flow rate of 125,000 pounds/hr, a temperature of 2° F., and a pressure of 450 psia. Partially purified ethylene is recovered in stream 2 at 96,785 pounds/hr at a temperature of −5.1° F. at a pressure of 350 psia. The partially purified ethylene stream includes 90.2 weight percent ethylene and 9.8 weight percent ethane. Partially purified ethane is recovered as stream 3 at 28,215 pounds per hour, a temperature of 31.4° F., and a pressure of 350 psia. The purified ethane stream includes 0.6 weight percent ethylene and 99.4 weight percent ethane.

To accomplish partial purification, the simulation indicates that a distillation tower is needed with a 12 foot diameter, a trayed section height of 84 feet, a reflux ratio of 2.5, and a refrigeration duty of 31.2 MM btu/hr. These results show that producing partially pure ethylene from the Crude C2 feed requires relatively small amounts of energy using a relatively small distillation column.

The ethylene partial purification simulation also shows that propylene, if present in the Crude C2 feed, is reduced to low levels in the resultant purified ethylene stream 2 while the ethylene is enriched. Propylene in the ethylene feed to hydroformylation tends to produce C4 compounds from the C3 compounds. The C4 compounds are difficult and costly to remove from the C3 compounds. It is preferable to have the propylene content in the ethylene product stream 2 to be below 0.1 wt. % to facilitate the production of C3 products with a purity of 99.9 wt % during subsequent hydroformylation. Partial purification can easily yield partially purified ethylene with this low level of C3 products. This shows that partial purification is substantially more economical to operate in terms of energy demand and the capital expense of the purification tower. Yet, the present invention teaches that such partially purified streams are even better for preparing C3 hydroformylation products than using higher purity streams in terms of overall capital cost and capacity.

Comparative Example 1

In a simulation, a typical, single or multi-staged, commercial hydroformylation reaction system is charged with pentanaldehyde, Rhodium carbon monoxide catalyst, and triphenyl phosphine. The system is brought to an appropriate temperature and pressure identical to Preferred Mode 5. In this example, a heated butane gas cycle stream containing ~75% butenes and some hydrogen are fed together with 1.1:1 $CO/H_2$ syngas continuously. The reaction temperature and feed rates are identical to Preferred Mode 5. Both liquid and a gas stream are removed continuously from the reaction system. The liquid phase is flashed at lower pressure to remove the bulk of the product pentanaldehydes. The reaction is non-selective in that both isopentaldehyde and n-pentaldehyde are produced. Butene conversion is less than 60% of that contained in the feed. Raising the reaction temperature raises conversion slightly, but as a tradeoffs makes the product stream less selective and results in less catalyst life.

Example 8

This example describes a simulation in which a feed mixture obtained from steam cracking ethane is distilled in order to prepare a partially purified ethylene stream. According to the simulation, a feed mixture obtained from steam cracking ethane is fed as stream 1 to a distillation tower. The feed stream 1 includes ethylene, ethane, propylene, propane, cis-butylene, butane, 2-methyl-1-buten, and benzene. The mass flow rate, pressure, temperature, and weight percent of the components in stream 1 are shown in the following Table 13-1.

TABLE 13-1

| | Stream No. | | |
|---|---|---|---|
| Stream Name | 1 Feed | 2 Ethylene | 3 Ethane + C3's |
| Overall Mass flow, lb/h | 125,000.0156 | 107,000.0313 | 18,000.0000 |
| Temp (F.) | 7.9998 | −0.5201 | 110.2888 |
| Pressure (psia) | 450.0000 | 375.0000 | 375.0000 |
| Component mass %: | | | |
| Ethylene | 78.304178 | 91.096038 | 2.263574 |
| Ethane | 11.253396 | 8.891729 | 25.292206 |
| Propylene | 1.424250 | 0.011623 | 9.821536 |
| Propane | 0.150616 | 0.000544 | 1.042709 |
| Cis-Butylene | 3.214359 | 0.000034 | 22.321750 |
| Butane | 1.398720 | 0.000020 | 9.713219 |
| 2-methyl-butene | 0.979990 | 0.000000 | 6.805488 |
| Benzene | 3.274489 | 0.000000 | 22.739519 |

Partially purified ethylene is recovered as stream 2 from the top of the column, which contains 91.1 weight percent ethylene. The mass flow rate, pressure, temperature, and weight percent of the components in stream 2 are shown in Table 13-1. Heavy components, some ethane, and some ethylene are recovered as stream 3 from the bottom of the distillation column. The mass flow rate, pressure, temperature, and weight percent of the components in stream 3 are shown in Table 13-1.

To accomplish this degree of partial purification of ethylene (91.9 weight percent ethylene in stream 2), the simulation indicates that a distillation tower is needed with 20 theoretical stages, a diameter of 10 feet, a reflux ratio of 1.4, a refrigeration duty of 18.6 MM BTU/hr, and a trayed section height of 40 feet. In contrast to the simulation in Comparative Example 2 where highly pure ethylene is recovered by distillation, the equipment and energy demands required for partial purification are substantially more modest.

Comparative Example 2

This example describes a comparative simulation in which a feed mixture obtained from steam cracking ethane is distilled in order to prepare a highly purified ethylene stream. According to the simulation, a feed mixture obtained from steam cracking ethane is fed as stream 1 to a distillation tower. The feed stream 1 includes ethylene, ethane, propylene, propane, cis-butylene, butane, 2-methyl-1-butene, and benzene as used in Example 8. The mass flow rate, pressure, temperature of the feed, and weight percent of the components in stream 1 is shown in Table CE2-1:

TABLE CE2-1

| | Stream No. | | |
|---|---|---|---|
| Stream Name | 1 Feed | 2 Ethylene | 3 Ethane + C3's |
| Overall Mass flow, lb/h | 125,000.0156 | 97,700.0078 | 27,300.0078 |
| Temp (F.) | 3.0000 | −1.1597 | 73.4433 |
| Pressure (psia) | 450.0000 | 385.0000 | 385.0000 |
| Component mass %: | | | |
| Ethylene | 78.304178 | 99.894452 | 1.037885 |
| Ethane | 11.253396 | 0.105541 | 51.148826 |
| Propylene | 1.424250 | 0.000000 | 6.521288 |
| Propane | 0.150616 | 0.000000 | 0.689633 |
| Cis-Butylene | 3.214359 | 0.000000 | 14.717759 |
| Butane | 1.398720 | 0.000000 | 6.404392 |
| 2-methyl-butene | 0.979990 | 0.000000 | 4.487132 |
| Benzene | 3.274489 | 0.000000 | 14.993079 |

Purified specification ethylene is recovered as stream 2 from the top of the column, which contains 99.9 weight percent ethylene. The mass flow rate, pressure, temperature of the feed, and weight percent of the components in stream 2 is shown in Table CE2-1. Heavy components, some ethane, and some ethylene are recovered as stream 3 from the bottom of the distillation column.

To accomplish this degree of essentially total purification of ethylene (99.9 weight percent ethylene in stream 2), the simulation indicates that a distillation tower is needed with 100 theoretical stages, a diameter of 15 feet, a reflux ratio of 3.9, a refrigeration duty of 46.3 MM BTU/hr, and a trayed section height of 216 feet. As shown by the simulation in this Comparative Example 2 where highly pure ethylene is recovered by distillation, the equipment and energy demands required for total specification purification are substantially more significant. In contrast to the simulation in Example 8 where partially pure ethylene is recovered by distillation, the equipment and energy demands required for high purification are substantially more modest.

Example 9

This example describes a simulation in which a feed mixture obtained from steam cracking ethane is distilled in order to prepare a partially purified ethylene stream. This partial purification is accomplished using the same distillation column used in Comparative Example 2. According to the simulation, a feed mixture obtained from steam cracking ethane is fed as stream 1 to a distillation tower. The feed stream 1 includes ethylene, ethane, propylene, propane, cis-butylene, butane, 2-methyl-1-butene, and benzene. The mass flow rate, pressure, temperature, and weight percent of the components in stream 1 are shown in Table 9-1:

TABLE 9-1

| Stream Name | Stream No. | | |
|---|---|---|---|
| | 1 Feed | 2 Ethylene | 3 Ethane + C3's |
| Overall Mass flow, lb/h | 373,520.0625 | 319,720.0313 | 53,800.0273 |
| Temp (F.) | 3.0000 | 1.2903 | 115.6407 |
| Pressure (psia) | 1200.0000 | 385.0000 | 385.0000 |
| Component mass %: | | | |
| Ethylene | 78.304178 | 91.316122 | 0.977481 |
| Ethane | 11.253396 | 8.666143 | 26.628795 |
| Propylene | 1.424250 | 0.017732 | 9.782828 |
| Propane | 0.150616 | 0.000000 | 1.045687 |
| Cis-Butylene | 3.214359 | 0.000000 | 22.316486 |
| Butane | 1.398719 | 0.000000 | 9.710958 |
| 2-methyl-butene | 0.979990 | 0.000000 | 6.803822 |
| Benzene | 3.274488 | 0.000000 | 22.733951 |

Partially purified ethylene is recovered as stream 2 from the top of the column, which contains 91.3 weight percent ethylene. The mass flow rate, pressure, temperature, and weight percent of the components in stream 2 are shown in Table 9-1. Heavy components, some ethane, and some ethylene are recovered as stream 3 from the bottom of the distillation column. The mass flow rate, pressure, temperature, and weight percent of the components in stream 3 are shown in Table 9-1.

Significantly, the simulation handles 373,520 lb/hr of feed to produce 319,720 lb/hr of a product stream including 91.3 weight percent of ethylene. Thus, the simulation prepares 319,720 lb/hr of partially purified ethylene using a refrigeration duty of only 16 mm BTU/hr. In contrast as shown in Comparative Example 2, the same column handles only 125,000 lb/hr of feed to produce 97,700 lb/hr of 99.9% pure ethylene and uses more energy (46.3 mm BTU/hr). This shows that the column throughput triples (3×) when using the column for partial purification with very little loss of ethylene! Also remarkably, this dramatic increase in throughput is accomplished using less energy and carries forward to allow hydroformylation throughput to be correspondingly tripled in as much as the distillation column is the limiting stage as between distillation and hydroformylation. The bottom line is that partial purification allows throughput to triple while using less energy as a process that attempts high purification of ethylene used for hydroformylation.

Example 10

This example describes a simulation in which a feed mixture obtained from steam cracking ethane is distilled in order to prepare a partially purified ethylene stream. This partial purification is accomplished using the same distillation column used in Comparative Example 2. According to the simulation, a feed mixture obtained from steam cracking ethane is fed as stream 1 to a distillation tower. The feed stream 1 includes ethylene, ethane, propylene, propane, cis-butylene, butane, 2-methyl-1-buten, and benzene. The mass flow rate, pressure, temperature, and weight percent of the components in stream 1 are shown in Table 10-1:

TABLE 10-1

| Stream Name | Stream No. | | |
|---|---|---|---|
| | 1 Feed | 2 Ethylene | 3 Ethane + C3's |
| Overall Mass flow, lb/h | 197,000.0156 | 161,800.0000 | 35,200.0313 |
| Temp (F.) | 3.0000 | 0.1814 | 87.5755 |
| Pressure (psia) | 450.0000 | 385.0000 | 385.0000 |
| Component mass %: | | | |
| Ethylene | 78.304183 | 95.131063 | 0.957938 |
| Ethane | 11.253397 | 4.868932 | 40.600139 |
| Propylene | 1.424250 | 0.000000 | 7.970937 |
| Propane | 0.150616 | 0.000000 | 0.842935 |
| Cis-Butylene | 3.214359 | 0.000000 | 17.989439 |
| Butane | 1.398720 | 0.000000 | 7.828055 |
| 2-methyl-butene | 0.979990 | 0.000000 | 5.484598 |
| Benzene | 3.274489 | 0.000000 | 18.325961 |

Partially purified ethylene is recovered as stream 2 from the top of the column, which contains 95.1 weight percent ethylene. The mass flow rate, pressure, temperature, and weight percent of the components in stream 2 are shown in Table 10-1. Heavy components, some ethane, and some ethylene are recovered as stream 3 from the bottom of the distillation column. The mass flow rate, pressure, temperature, and weight percent of the components in stream 3 are shown in Table 10-1.

Significantly, the simulation handles 197,000 lb/hr of feed to produce 162,750 lb/hr of a product stream including 95.1 weight percent of ethylene. Thus, the simulation prepares 162,750 lb/hr of partially purified ethylene using a refrigeration duty of only 36.4 mm BTU/hr.

In contrast as shown in Comparative Example 2, the same column handles only 125,000 lb/hr of feed to produce 97,700 lb/hr of 99.9% pure ethylene and uses more energy (46.3 mm BTU/hr). This shows that the column throughput nearly doubles (2×) when using the column for partial purification with very little loss of ethylene! Also remarkably, this dramatic increase in throughput is accomplished using less energy and carries forward to allow hydroformylation throughput to be correspondingly doubled in as much as the distillation column is the limiting stage as between distillation and hydroformylation. The bottom line is that partial purification allows throughput to double while using less energy than a process that attempts high purification of ethylene used for hydroformylation.

All patents, patent applications, and publications cited herein are incorporated by reference as if individually incorporated. Unless otherwise indicated, all parts and percentages are by weight and all molecular weights are number average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:
1. A method of using ethylene, comprising the steps of:
    (a) providing a crude feed mixture comprising ethane and ethylene;
    (b) partially purifying the crude feed mixture in a manner effective to provide a partially purified feed mixture comprising 80 to 98 weight percent of ethylene based on the total weight of hydrocarbons in the partially purified feed mixture and having less than 2 weight % C3 and higher hydrocarbons in the feed mixture based on the total weight of hydrocarbons in the feed mixture;
(c) contacting the partially purified feed mixture with a gas mixture comprising hydrogen and carbon monoxide in the presence of a catalyst under hydroformylation conditions in a plurality of reactor zones to convert at least a portion of the ethylene in the partially purified feed mixture into a product mixture comprising propionaldehyde and ethane;
(d) recovering a first product mixture portion from the product mixture, said first product mixture portion comprising a major portion of the propionaldehyde prepared in step (c); and
(e) recovering a second product mixture portion from the product mixture, said second product mixture portion comprising a major portion of the ethane in the product mixture.

2. The method of claim 1, wherein the plurality of reactor zones comprises first and second reactor zones, and wherein a first reaction vessel comprises the first reaction zone and a second reaction vessel comprises the second reaction zone.

3. The method of claim 1, wherein the plurality of reactor zones comprises first and second reactor zones, and wherein a single reaction vessel comprises the first and second reactor zones.

4. The method of claim 1, wherein the partially purified feed mixture comprises gaseous ethylene and wherein step (c) comprises contacting the gaseous ethylene with a liquid phase that contains a Rh catalyst.

5. The method of claim 1, wherein a portion of step (c) occurs in a first reactor such that more than 70% by weight of the ethylene in the partially purified feed mixture is converted to the product mixture and remaining ethylene, and wherein a portion of step (c) occurs in a second reactor such that more than 70% by weight of the remaining ethylene in the product mixture is converted to the product mixture.

6. The method of claim 1, wherein the partially purified ethylene mixture provided in step (b) comprises less than 0.5 weight percent C3 and higher hydrocarbons and wherein greater than 99 weight percent of the olefin content is ethylene.

7. The method of claim 1, further comprising the step causing at least a portion of the ethane in the second product mixture to be burned as a fuel.

8. The method of claim 1, wherein step (a) comprises hydrogenating the crude feed mixture.

9. The method of claim 1, wherein step (b) comprises hydrogenating the partially purified feed mixture.

10. The method of claim 1, wherein the feed mixture of step (a) comprises 10 to 75 weight percent of ethylene based on the total weight of hydrocarbons in the feed mixture.

11. The method of claim 1 wherein the second product mixture portion comprises ethane, CO, and hydrogen, and wherein at least a portion of the ethane, CO and/or hydrogen in the second product mixture portion is used to prepare the carbon monoxide and hydrogen used in step (c).

12. The method of claim 1, further comprising the step of reducing the propionaldehyde to provide 1-propanol.

13. The method of claim 12, further comprising the step of dehydrating the 1-propanol to provide propylene.

14. The method of claim 13, further comprising the step of using the propylene to provide polypropylene.

15. The method of claim 1, wherein the partially purified feed mixture provided in step (b) is substantially all ethane and ethylene.

16. The method of claim 1, wherein the crude feed mixture of step (a) comprises ethylene and ethane, wherein the weight ratio of the ethane to the ethylene in the crude feed mixture is in the range from 1:10 to 4:1; and wherein the partially purified feed mixture provided in step (b) comprises ethane and ethylene, wherein the weight ratio of the ethane to the ethylene in the partially purified feed mixture is in the range from 1:70 to 1:4.

17. The method of claim 1, wherein a portion of a syngas comprising CO and hydrogen is used in step (c) and wherein the method further comprises the step of using a portion of the hydrogen of the syngas to reduce the propionaldehyde to 1-propanol.

18. The method of claim 1, wherein the partially purified ethylene feed mixture comprises 90 to 98 weight percent ethylene based on the total amount of hydrocarbons in the partially purified feed mixture.

19. The method of claim 1, wherein the partially purified ethylene feed mixture comprises 85 to 98 weight percent ethylene based on the total amount of hydrocarbons in the partially purified feed mixture.

20. The method of claim 1, wherein the crude feed mixture of step (a) further comprises light and heavy components and wherein step (b) further comprises removing at least 99 weight percent of the light and heavy components of the crude feed mixture.

21. The method of claim 1, wherein step (c) occurs in the presence of a catalyst comprising rhodium.

22. The method of claim 1, wherein step (c) occurs in the presence of a catalyst comprising rhodium in a complex combination with CO, hydrogen, and an organo phosphorous containing ligand.

* * * * *